United States Patent
Lourdusamy et al.

(10) Patent No.: US 8,207,358 B2
(45) Date of Patent: Jun. 26, 2012

(54) METHODS FOR THE PREPARATION OF TAXANES USING CHIRAL AUXILIARIES

(75) Inventors: Mettilda Lourdusamy, Sainte-foy (CA); Gaétan Caron, Québec (CA)

(73) Assignee: Accord Healthcare Ltd., Markham, Ontario (CA)

( * ) Notice: Subject to any disclaimer, the term of this patent is extended or adjusted under 35 U.S.C. 154(b) by 766 days.

(21) Appl. No.: 12/092,432

(22) PCT Filed: Nov. 3, 2006

(86) PCT No.: PCT/CA2006/001806
§ 371 (c)(1),
(2), (4) Date: Jul. 22, 2008

(87) PCT Pub. No.: WO2007/051306
PCT Pub. Date: May 10, 2007

(65) Prior Publication Data
US 2009/0137796 A1     May 28, 2009

Related U.S. Application Data

(60) Provisional application No. 60/733,172, filed on Nov. 4, 2005.

(51) Int. Cl.
*C07D 305/00* (2006.01)
*C07D 407/00* (2006.01)
(52) U.S. Cl. ...................................... 549/510; 549/511
(58) Field of Classification Search .................. 549/510, 549/511
See application file for complete search history.

(56) References Cited

U.S. PATENT DOCUMENTS

| 4,156,684 | A  | 5/1979  | Crutcher         |
|-----------|----|---------|------------------|
| 5,637,732 | A  | 6/1997  | Holton et al.    |
| 5,705,508 | A  | 1/1998  | Ojima et al.     |
| 5,889,043 | A  | 3/1999  | Bouchard et al.  |
| 6,090,951 | A  | 7/2000  | Poss et al.      |
| 6,127,355 | A  | 10/2000 | Greenwald et al. |
| 6,281,368 | B1 | 8/2001  | McChesney et al. |
| 6,495,705 | B2 | 12/2002 | Chander et al.   |
| 6,861,537 | B2 | 3/2005  | Holton et al.    |
| 2001/0053857 | A1 | 12/2001 | Holton et al. |
| 2004/0225009 | A1 | 11/2004 | Kadow et al. |
| 2005/0288520 | A1 | 12/2005 | Naidu |

FOREIGN PATENT DOCUMENTS

| FR | 2121387 | 8/1972 |
| WO | WO 00/09073 A2 | 2/2000 |
| WO | WO 2006/102758 A1 | 10/2006 |

OTHER PUBLICATIONS

Form PCT/ISA/210 (International Search Report) dated Feb. 15, 2007.
De Groot et al. *Angew. Chem.. Int.*, Ed. 2003, vol. 42, pp. 4490-4494.
Greenwald et al. *Journal of Medical Chemistry*, (1996) vol. 39, pp. 424-431.
Sudo et al., *Macromolecules*, (1998) vol. 31, pp. 7996-7998.
Wen et al., *J. Org. Chem* (2002) vol. 67, No. 22, pp. 7887-7889.

*Primary Examiner* — Andrew D Kosar
*Assistant Examiner* — Raymond Covington
(74) *Attorney, Agent, or Firm* — Buchanan Ingersoll & Rooney

(57) ABSTRACT

The present invention relates to a stereoselective synthesis of novel β-lactam dimers as useful precursors for the preparation of paclitaxel, docetaxel, and analogues thereof. More particularly, the new β-lactams are prepared from readily available and enantiomerically pure chiral auxiliaries. The β-lactams are then reacted with a suitably protected taxane to produce diastereomerically enriched side chain-bearing taxanes. Finally, the chiral auxiliary is cleaved and protecting groups are removed to provide the desired taxane.

69 Claims, No Drawings

METHODS FOR THE PREPARATION OF TAXANES USING CHIRAL AUXILIARIES

CROSS-REFERENCE TO RELATED APPLICATIONS

This application claims the benefit of U.S. provisional application No. 60/733,172 filed Nov. 4, 2005 which is incorporated herein by reference in its entirety.

TECHNICAL FIELD

The present invention is directed towards novel β-lactams used as starting material for the synthesis of taxanes. The novel β-lactams are chiral and are prepared by enantioselective synthesis using chiral auxiliaries. The present invention is also directed towards the use of the new β-lactams to convert 10-deacetylbaccatin III and 9-dihydro-13-acetylbaccatin III to paclitaxel, docetaxel and analogs thereof.

BACKGROUND OF THE INVENTION

Paclitaxel, a naturally occurring diterpenoid extracted from yew trees, has demonstrated great potential as an anticancer drug. It is unique among antimitotic drugs in that it promotes the assembly of stable microtubules from tubulin. It binds strongly to microtubules, thus preventing depolymerization of the tubulin and inhibiting mitosis. The structure of paclitaxel and the numbering system conventionally used is shown below. This numbering system is also applicable to compounds used in the process of the present invention.

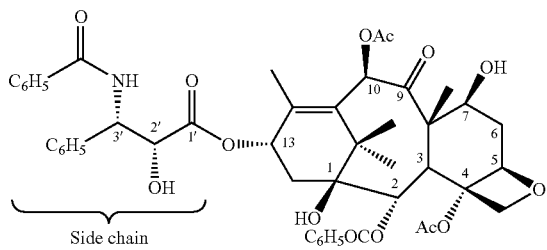

Docetaxel, a paclitaxel derivative, has also demonstrated excellent antitumor activity over the past few years. Docetaxel has the following structure:

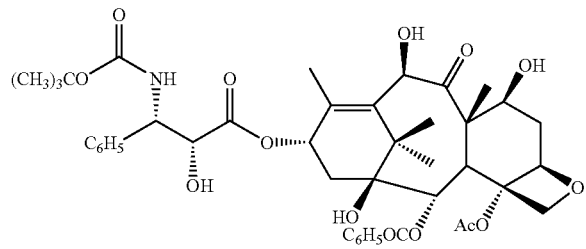

The chemical conversion of naturally occurring precursors such as 10-deacetylbaccatin III (10-DAB III) and 9-dihydro-13-acetylbaccatin III (9-DHAB III) to paclitaxel and docetaxel have been reported. Because of the congested position of the 13-hydroxy group of 10-DAB-III and 9-DHAB-III, acylation with β-lactam has become the method of choice for acylation of that position. An example of β-lactam which has been extensively used in the synthesis of paclitaxel and docetaxel is shown below:

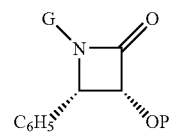

where G is a benzoyl group when preparing paclitaxel or a tert-butyloxycarbonyl (t-BOC) group when preparing docetaxel and P is a "classical" hydroxy protecting group such as TES, methyloxypropyl and 2,2,2-trichloroethoxycarbonyl.

An important limitation of the current method is that although the syn lactam can be obtained by methods such as the Staudinger reaction, the racemic form is always produced. The racemic mixture must be submitted to a kinetic resolution either prior to or during coupling with baccatin III. In either case half of the lactam material must be discarded. A chiral synthesis of β-lactams would produce the desired isomer stereoselectively but few such synthetic routes have been developed.

It would thus be highly desirable to be provided with new routes for the enantioselective production of chiral β-lactams and new methods to use such β-lactams in the synthesis of paclitaxel, docetaxel and other biologically active taxanes.

SUMMARY OF THE INVENTION

In one aspect the present invention provides a process for the preparation of paclitaxel, docetaxel, and analogs thereof where novel β-lactams of formula I:

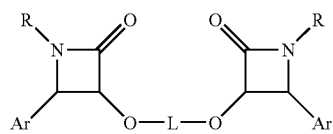

wherein R, Ar and L are as defined herein are reacted with a suitable taxane precursor having a free C-13 hydroxy group.

In accordance with another aspect of the present invention, there is provided novel β-lactams of formula I and methods of preparation thereof:

wherein R, Ar and L are as defined herein.

In accordance with another aspect of the present invention, there is provided a compound of formula V and methods of preparation thereof:

V

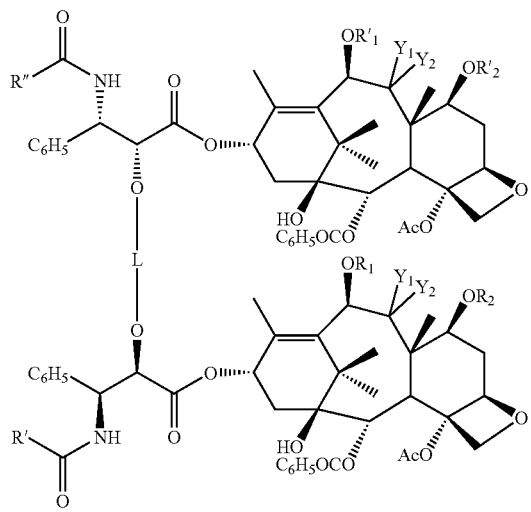

wherein R', R" L, $R_1$, $R_2$, $R'_1$, $R'_2$, $Y_1$ and $Y_2$ are as defined herein.

In accordance with another aspect of the present invention, there is provided a compound of formula VII

VII

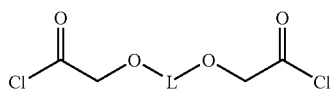

wherein L is as defined herein.

DETAILED DESCRIPTION OF THE PREFERRED EMBODIMENT

In accordance with one embodiment, there is provided β-lactam of formula I:

I

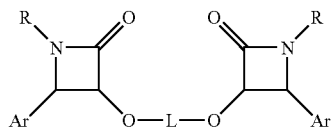

wherein R is hydrogen, aryl or acyl, Ar is an aryl and L is a cleavable linker, and more preferably a chiral auxiliary (linker).

In one embodiment, there is provided a compound of formula I

I

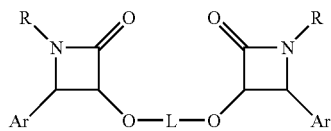

in racemic or in either isomerically pure form, wherein R is hydrogen, aryl or acyl, Ar is aryl, and L is a cleavable linker, chiral or non chiral, preferably selected from the group consisting of hydrolysable ketals, acetals, silyl, esters, diesters, and hydrogenolyzable benzyl group.

In further embodiments, there is provided a compound of formula I wherein:
R is hydrogen;
R is p-methoxyphenyl;
R is benzoyl; or
R is tert-butyloxycarbonyl (t-BOC).

In one embodiment, there is provided a compound of formula I wherein Ar is aryl having 6 carbon atoms and which may be optionally substituted with one or more substituents. In one embodiment, Ar is phenyl optionally substituted with one or more substituents. In a further embodiment, Ar is unsubstituted phenyl.

Still in accordance with the present invention, there is provided β-lactams of the formula I in which chiral centers of the β-lactam moieties are optically pure or stereochemically enriched by using a chiral auxiliary as the L group during their preparation. Stereochemically enriched β-lactams of formula I can be used as intermediates in the synthesis of biologically active taxanes such as paclitaxel, docetaxel and analogs thereof. In such syntheses, β-lactams of formula I are superior to racemic ones in that less starting material is required and only the desired taxane isomer is generated.

One advantage of the β-lactams of formula I is that the chiral linker L can be cleaved efficiently to provide side chain-bearing taxanes.

Another advantage of the β-lactams of formula I for taxane synthesis is that their dimeric forms provide additional steric hindrance during coupling reactions to baccatin III compounds which in turns results in increased kinetic resolution during coupling and better diastereomeric excess of the coupling products. Simple non chiral linkers can also be used in instances where the additional steric bulk provided by structures of formula I generates sufficient kinetic resolution during the coupling reaction to taxanes.

In one embodiment, there is provided a compound of formula V

V

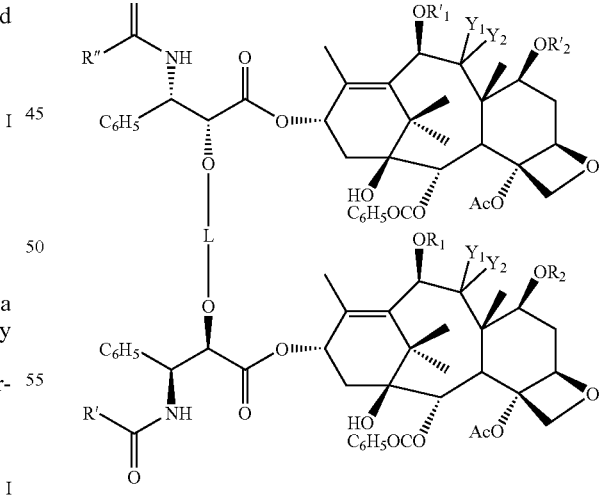

wherein R' and R", identical or different, are independently aryl, alkyl or alkyloxy, $R_1$, $R'_1$, $R_2$ and $R'_2$, identical or different, are independently acyl, hydrogen or a hydroxy protecting group, L is a cleavable linker, and more preferably a chiral linker, $Y_1$ is a hydroxy or a protected hydroxy group, $Y_2$ is a hydrogen or a protected hydroxy group or $Y_1$ and $Y_2$ taken together form a carbonyl group.

It is understood that the two molecules linked by the linker need not to be identical. They may preferably be, but they alternatively may be different. The present invention is to include both possibility, as one skilled in the art will appreciate that both possibilities may be useful.

In one embodiment, there is provided a compound of formula IIa or IIb

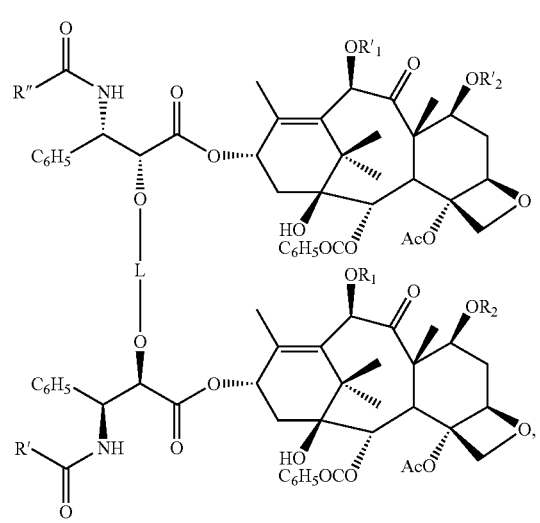

IIa

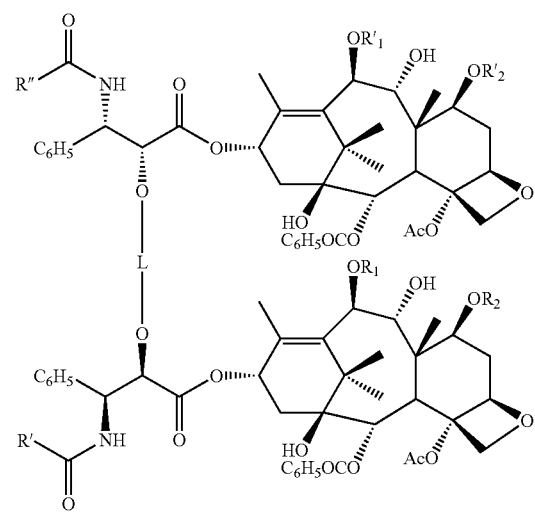

IIb wherein R' and R", identical or different, are independently aryl, alkyl or alkyloxy, $R_1$, $R'_1$, $R_2$ and $R'_2$, identical or different, are independently acyl, hydrogen or a hydroxy protecting group, L is a cleavable linker, and more preferably a chiral linker, $Y_1$ is hydrogen, a hydroxy or a protected hydroxy group, $Y_2$ is a hydrogen or a protected hydroxy group or $Y_1$ and $Y_2$ taken together form a carbonyl group.

In one embodiment there is provided a compound of formula VI

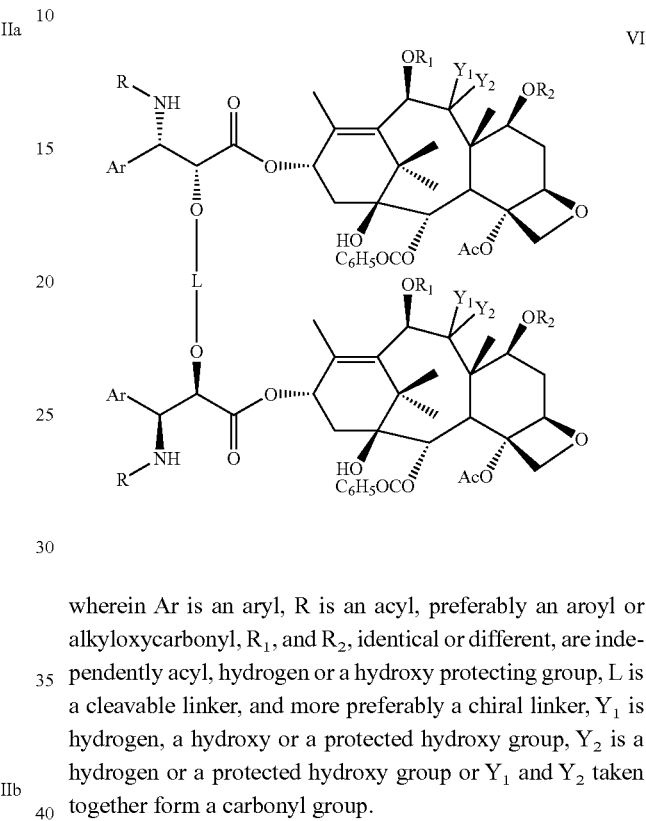

VI wherein Ar is an aryl, R is an acyl, preferably an aroyl or alkyloxycarbonyl, $R_1$, and $R_2$, identical or different, are independently acyl, hydrogen or a hydroxy protecting group, L is a cleavable linker, and more preferably a chiral linker, $Y_1$ is hydrogen, a hydroxy or a protected hydroxy group, $Y_2$ is a hydrogen or a protected hydroxy group or $Y_1$ and $Y_2$ taken together form a carbonyl group.

In one embodiment, there is provided a compound of formula VIa or VIb

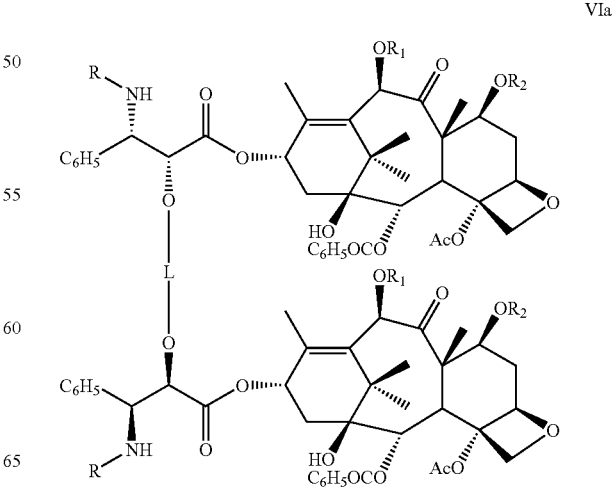

VIa

-continued

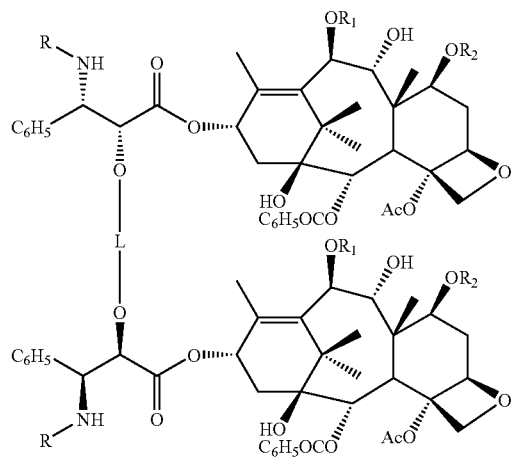

wherein R is benzoyl or tert-butyloxycarbonyl, $R_1$ and $R_2$, identical or different, are independently hydrogen, acyl or hydroxy protecting group and L is a cleavable linker, chiral or non chiral, preferably selected from the group consisting of hydrolysable ketals, acetals, silyl, diesters, and hydrogenolyzable benzyl group.

In one embodiment, there is provided a compound of formula VI, VIa or VIb wherein R is benzoyl, $R_1$ is acetyl and $R_2$ is a hydroxy protecting group.

In one embodiment, $R_2$ is selected from the group consisting of ethoxyethyl, triethylsilyl, triisopropylsilyl, t-butyldimethylsilyl, t-butyldiphenylsilyl, benzyl and tert-butyloxycarbonyl and R is benzoyl or tert-butyloxycarbonyl. Preferably $R_2$ is triethylsilyl.

In further embodiments, there is provided a compound of formula VI, VIa or VIb wherein:
R is benzoyl, $R_1$ is acetyl and $R_2$ is a hydrogen;
R is benzoyl and $R_1$ and $R_2$ are both hydrogen;
R is benzoyl and $R_1$ and $R_2$ are both a hydroxy protecting group.

In further embodiments, there is provided a compound of formula VI, VIa or VIb wherein $R_1$ and $R_2$ are selected from the group consisting of ethoxyethyl, triethylsilyl, triisopropylsilyl, t-butyldimethylsilyl, t-butyldiphenylsilyl, benzyl and tert-butyloxycarbonyl and R is benzoyl or tert-butyloxycarbonyl. Preferably $R_1$ and $R_2$ are triethylsilyl.

In one embodiment, there is provided compounds of formula VI, VIa or VIb wherein R is tert-butyloxycarbonyl, $R_1$ is acetyl and $R_2$ is a hydroxy protecting group. Preferably, $R_1$ and $R_2$ are triethylsilyl.

In further embodiments, there is provided a compound of formula VI, VIa or VIb wherein $R_2$ is selected from the group consisting of ethoxyethyl, triethylsilyl, triisopropylsilyl, t-butyldimethylsilyl, t-butyldiphenylsilyl, benzyl and tert-butyloxycarbonyl and R is benzoyl or tert-butyloxycarbonyl.

In further embodiments, there is provided a compound of formula VI, VIa or VIb wherein:
R is tert-butyloxycarbonyl, $R_1$ is acetyl and $R_2$ is a hydrogen;
R is tert-butyloxycarbonyl and $R_1$ and $R_2$ are both hydrogen;
R is tert-butyloxycarbonyl and $R_1$ and $R_2$ are both a hydroxy protecting group;
$R_1$ and $R_2$ are selected from the group consisting of ethoxyethyl, triethylsilyl, triisopropylsilyl, t-butyldimethylsilyl, t-butyldiphenylsilyl, benzyl and tert-butyloxycarbonyl and R is benzoyl or tert-butyloxycarbonyl.

In one embodiment, there is provided a compound of formula VII

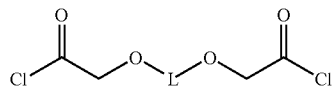

wherein L is a cleavable linker, chiral or non chiral, selected from the group consisting of hydrolysable ketals, acetals, silyl, diesters, and hydrogenolyzable benzyl group.

In further embodiments of the invention, there is provided a compound of formula I, IIa, IIb, V, VI, VIa, VIb or VII wherein:
L is a cleavable chiral auxiliary;
L is a chiral tartaric diester acetonide having enantiomerically enriched or substantially pure (R,R) or (S,S) stereochemistry, or a mixture of (R,R) and (S,S) enantiomers including racemic mixtures;
L is a chiral trans-1,2-cyclohexane di(carboxylate ester) having enantiomerically enriched or substantially pure (R,R) or (S,S) stereochemistry or a mixture of (R,R) and (S,S) enantiomers including racemic mixtures;
L is a chiral 1,1'-binaphthyl-2,2'-di(carboxylate ester) having enantiomerically enriched or substantially pure (R) or (S) stereochemistry or a mixture of (R) and (S) enantiomers including racemic mixtures.

In a further embodiment, there is provided a compound of formula I, IIa, IIb, V, VI, VIa, VIb or VII wherein L is a ketal or acetal of formula

wherein Rc and R'c, identical or different are alkyl, aryl or hydrogen.

In further embodiments, Rc and R'c are independently an alkyl of 1 to 6 carbon atoms, Rc and R'c are independently an alkyl of 1 to 3 carbon atoms; Rc and R'c are independently an alkyl of 1 carbon atom; Rc and R'c are a methyl group; Rc and R'c form together a cyclic alkyl ring of 3 to 6 carbon atoms.

In further embodiments, Rc and R'c are independently an aryl having 6 to 10 carbon atoms and which may be optionally substituted with one or more substituents; Rc and R'c are independently an aryl having 6 carbon atoms; Rc and R'c are a phenyl optionally substituted with one or more substituents. In a further embodiment, Rc and R'c are unsubstituted phenyl.

In a further embodiment, there is provided a compound of formula I, IIa, IIb, V, VI, VIa, VIb or VII wherein L is a silyl linker of formula

wherein Rd and R'd, identical or different are alkyl, aryl or hydrogen.

In further embodiments, Rd and R'd are independently an alkyl of 1 to 6 carbon atoms, Rd and R'd are independently an alkyl of 1 to 3 carbon atoms; Rd and R'd are independently an alkyl of 1 carbon atom; Rd and R'd are a methyl group; Rd and R'd form together a cyclic alkyl ring of 3 to 6 carbon atoms.

In further embodiments, Rd and R'd are independently an aryl having 6 to 10 carbon atoms and which may be optionally substituted with one or more substituents; Rd and R'd are independently an aryl having 6 carbon atoms; Rd and R'd are a phenyl optionally substituted with one or more substituents. In a further embodiment, Rd and R'd are unsubstituted phenyl.

In a further embodiment, there is provided a compound of formula I, IIa, IIb, V, VI, VIa, VIb or VII wherein L is a linker of formula

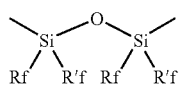

wherein Rf and R'f, identical or different are alkyl, aryl or hydrogen.

In further embodiments, Rf and R'f are independently an alkyl of 1 to 6 carbon atoms, Rf and R'f are independently an alkyl of 1 to 3 carbon atoms; Rf and R'f are independently an alkyl of 1 carbon atom; Rf and R'f are a methyl group; Rf and R'f form together a cyclic alkyl ring of 3 to 6 carbon atoms.

In further embodiments, Rf and R'f are independently an aryl having 6 to 10 carbon atoms and which may be optionally substituted with one or more substituents; Rf and R'f are independently an aryl having 6 carbon atoms; Rf and R'f are a phenyl optionally substituted with one or more substituents. In a further embodiment, Rf and R'f are unsubstituted phenyl.

In a further embodiment, there is provided a compound of formula I, IIa, IIb, V, VI, VIa, VIb or VII wherein L is a linker of formula

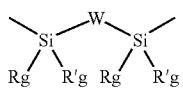

wherein Rg and R'g, identical or different are alkyl, aryl or hydrogen; W is an alkyl.

In further embodiments, W is an alkyl of 1 to 30 carbon atoms, preferably 1 to 10 carbon atoms, more preferably 1 to 6 carbon atoms. More preferably, W is —$(CH_2)_n$— wherein n is 1 to 30, alternatively, n is 1 to 10 or 1 to 6.

In further embodiments, Rg and R'g are independently an alkyl of 1 to 6 carbon atoms, Rg and R'g are independently an alkyl of 1 to 3 carbon atoms; Rg and R'g are independently an alkyl of 1 carbon atom; Rg and R'g are a methyl group; Rg and R'g form together a cyclic alkyl ring of 3 to 6 carbon atoms.

In further embodiments, Rg and R'g are independently an aryl having 6 to 10 carbon atoms and which may be optionally substituted with one or more substituents; Rg and R'g are independently an aryl having 6 carbon atoms; Rg and R'g are a phenyl optionally substituted with one or more substituents. In a further embodiment, Rg and R'g are unsubstituted phenyl.

In a further embodiment, there is provided a compound of formula I, IIa, IIb, V, VI, VIa, VIb or VII wherein L is —$CH_2$—$(C_6H_5)$—$(CH_2)$—.

In one embodiment, the present invention provides a compound of formula III

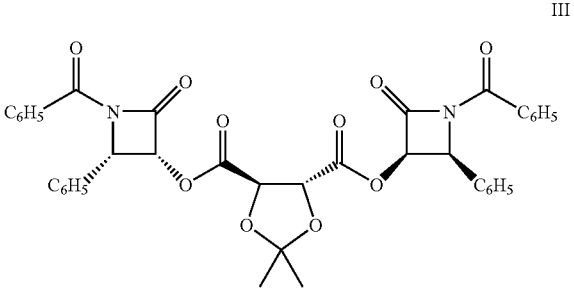

where the L group of compound of formula I is now an optically pure chiral tartrate acetonide group. The compound of formula III can be used in the synthesis of paclitaxel.

In another preferred embodiment, the present invention provides a compound of formula IV

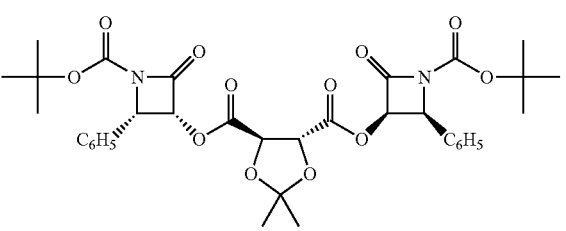

Compound of formula IV can be used in the synthesis of docetaxel.

Taxane precursors having a free C-13 hydroxy group suitable for use in the present invention are not particularly limited. An example of suitable taxane structure includes compounds defined by the general formula

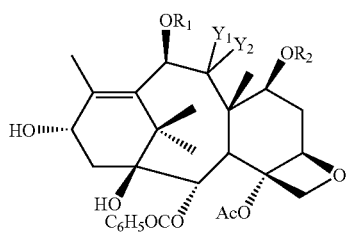

wherein $R_1$, $R_2$, $Y_1$ and $Y_2$ are as defined herein above. Preferably $R_1$ and $R_2$ are a hydroxy protecting group and more preferably a triethylsilyl. Alternatively, $R_1$ is an acyl, preferably an acetyl group, and $R_2$ is a hydroxy protecting group, preferably a triethylsilyl. Preferably, $Y_1$ is a hydroxyl and $Y_2$ is a hydrogen More preferably $Y_1$ is a hydroxyl having stereochemistry

Alternatively, $Y_1$ and $Y_2$ taken together form a carbonyl group.

Examples of taxane precursors useful to practice the present invention are described in WO 2006/102758, the content of which is hereby incorporated by reference.

For the purpose of the present invention the following terms are defined below.

The term "hydroxy protecting group" is intended to mean a group that is attached to the oxygen of the hydroxyl group, for protecting said group from reacting in a subsequent reaction. Such group are well known in the art and examples include without limitation ethoxyethyl, triethylsilyl, triisopropylsilyl, t-butyldimethylsilyl, t-butyldiphenylsilyl, benzyl and tert-butyloxycarbonyl. Preferably, the protecting group is triethylsilyl.

The term "alkyl" represents a linear, branched or cyclic hydrocarbon moiety having 1 to 30 carbon atoms, preferably 1 to 12 and more preferably 1 to 6, which is optionally substituted. Examples include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, cyclopropyl, cyclobutyl, cyclopentyl and cyclohexyl. The term alkyl is also meant to include alkyls in which one or more hydrogen atom is replaced by a halogen, ie. an alkylhalide. Examples include but are not limited to mono or polyfluorinated alkyl or mono or polychlorinated alkyl such as trifluoromethyl, trichloromethyl, trifluoroethyl, trichloroethyl. The expression "lower alkyl" refers to alkoxy having 1 to 3 carbon atoms.

The term "alkyloxy" represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy. The expression "lower alkoxy" refers to alkoxy having 1 to 3 carbon atoms.

The term "acyl" is defined as a radical derived from a carboxylic acid, obtained by replacement of the —OH group. Like the acid to which it is related, an acyl radical may be linear, branched or cyclic alkyl, alkyloxy or aryl, which are optionally substituted. Examples include but are not limited to formyl, acetyl, propionyl, butyryl, alkyloxycarbonyl (such as terbutyloxycarbonyl), isobutyryl, valeryl, isovaleryl, pivaloyl, caproyl, isocaproyl, acryloyl, propioloyl, methacryloyl, crotonoyl, isocrotonoyl, aroyls (such as benzoyl, naphthoyl, toluoyl, cinnamoyl), furoyl, glyceroyl, salicyloyl.

The term "aryl" represents a carbocyclic moiety containing one benzenoid-type ring having 6 to 14 carbon atoms, preferably 6 to 10 carbon atoms, more preferably 6 carbon atoms and which may be optionally substituted with one or more substituents. Examples include but are not limited to phenyl, tolyl, dimethyphenyl, aminophenyl, anilinyl.

The term "independently" means that a substituent can be the same or a different definition for each item.

The terms "substituted" or "substituent" represent one or more halogen, amino, cyano, hydroxyl, nitro, acyl or —O-acyl, lower alkyl or lower alkoxy; preferably, halogen, lower alkyl or lower alkoxy.

The terms "leaving group" is an atom or molecule that detaches from the parent compound. Examples include halogen such as chloride, bromide and iodide, anhydrides such as an acetoxy or a group derived from the parent compound such as a succinimide, a pyridinium or an amino pyridinium such as dimethylaminopyridinium.

There is also provided "enantiomers" of the present invention. It will be appreciated that the compounds in accordance with the present invention can contain a chiral center. The compounds in accordance with the present invention may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present invention can contain more than one chiral centres. The compounds of the present invention may thus exist in the form of different diastereomers. All such diastereomers and mixtures thereof are included within the scope of the invention. The single diastereomer can be obtained by method well known in the art, such as HPLC, crystalisation and chromatography.

The terms "isomerically pure form" with reference to enantiomers of the compounds of the invention means enantiomerically enriched or substantially pure enantiomers or with reference to diastereomers of the compounds of the invention means diastereomerically enriched or substantially pure diastereomers.

In another embodiment, the present invention also provides a process for the preparation of compounds of formula I from chiral auxiliaries. The present invention also provides a process for the use of a compound of formula I in the synthesis of taxanes.

In one embodiment, there is provided a process for producing a compound of formula 5″

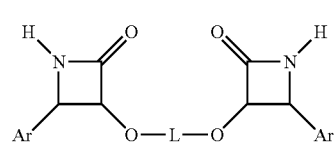

wherein Ar is an aryl group and L is a cleavable linker, chiral or non chiral, preferably selected from the group consisting of hydrolysable ketals, acetals, silyl, diesters, and hydrogenolyzable benzyl group,
comprising reacting a compound of formula 3'

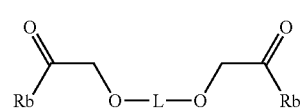

wherein Rb is an alkyloxy and L is as defined above, with a compound of formula

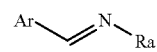

wherein Ar is as defined above and Ra is a group cleaveable in situ from the reaction condition or from an isolation process.

In further embodiments:
Rb is an alkyloxy of 1 to 12 carbon atoms,
Rb is an alkyloxy of 1 to 6 carbon atoms,
Rb is an alkyloxy of 1 to 3 carbon atoms,
Rb is a methoxy or an ethoxy.

In further embodiments:
Ra is a trialkyl silyl, wherein each of the alkyl is independently selected and is a linear or branched alkyl of 1 to 4 carbon atoms;
Ra is a trimethyl silyl;
Ra is a triethyl silyl
Ra is a triisopropylsilyl;
Ra is a t-butyldimethylsilyl;
Ra is a t-butyldiphenylsilyl.

In one embodiment, there is provided a process comprising reacting a compound of formula

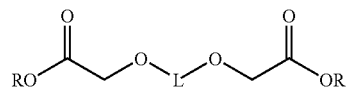

wherein R is alkyl, with a compound of formula

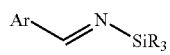

so as to provide a compound of formula

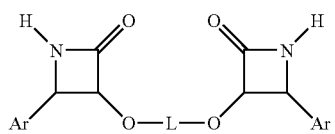

chiral or racemic, wherein Ar is an aryl group and L is a cleavable linker, chiral or non chiral, preferably selected from the group consisting of hydrolysable ketals, acetals, silyl, diesters, and hydrogenolyzable benzyl group.

In one embodiment, there is provided a process for producing a compound of formula 5'

wherein Ar is an aryl group and L is a cleavable linker, chiral or non chiral, preferably selected from the group consisting of hydrolysable ketals, acetals, silyl, diesters, and hydrogenolyzable benzyl group; Ra is a group cleaveable under oxydative condition;
comprising reacting a compound of formula 3'

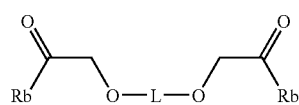

wherein Rb is leaving group and L is as defined above, with a compound of formula

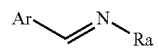

wherein Ar and Ra are as defined above.
In further embodiments,
Ra is 4-methoxyphenyl;
Rb is a chloride, a bromide or an iodide;
Ra is 4-methoxyphenyl and Rb is a chloride.

In one embodiment, there is provided a process comprising reacting a compound of formula

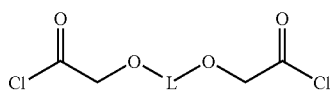

with a compound of formula

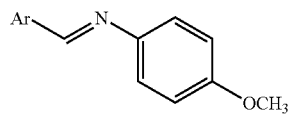

so as to provide a compound of formula

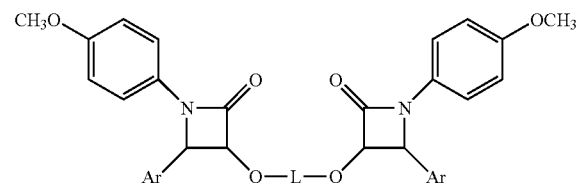

chiral or racemic, wherein Ar is an aryl group and L is a cleavable linker, chiral or non chiral, preferably selected from the group consisting of hydrolysable ketals, acetals, silyl, diesters, and hydrogenatable benzyl group.

In one embodiment, there is provided a process for producing a compound of formula 5"

wherein Ar is an aryl group and L is a cleavable linker, chiral or non chiral, preferably selected from the group consisting of hydrolysable ketals, acetals, silyl, diesters, and hydrogenolyzable benzyl group,
comprising reacting a compound of formula 5'

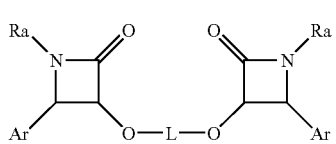

with an oxidant reagent, wherein Ar and L are as defined above and Ra is a group cleavable under oxydative condition.

In one embodiment, the oxidant reagent is ceric (IV) ammonium nitrate.

In a further embodiment, Ra is 4-methoxyphenyl.

In still a further embodiment there is provided a process comprising oxidation of a compound of formula

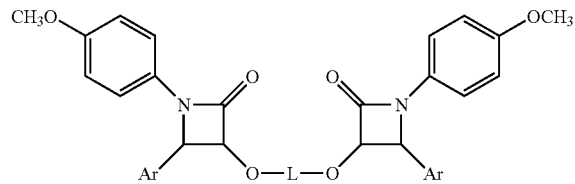

using an oxidizing agent to provide a compound of formula

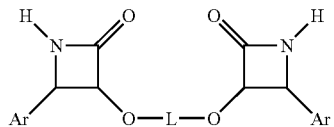

chiral or racemic, wherein Ar is an aryl group and L is a cleavable linker, chiral or non chiral, preferably selected from the group consisting of hydrolysable ketals, acetals, silyl, diesters, and hydrogenolyzable benzyl group.

In one embodiment, there is provided a process for producing a compound of formula 5'''

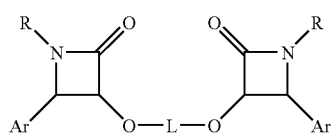

wherein Ar is an aryl group and L is a cleavable linker, chiral or non chiral, preferably selected from the group consisting of hydrolysable ketals, acetals, silyl, diesters, and hydrogenolyzable benzyl group, R is an acyl group; preferably an aroyl or alkyloxycarbonyl, comprising treating a compound of formula 5"

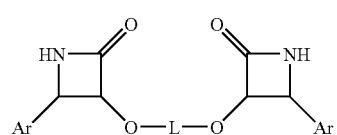

wherein Ar and L are as described above, with an acylating agent to produce compound of formula 5'''.

In one embodiment, R is a tert-butyloxycarbonyl or a benzoyl. In a further embodiment, the acylating agent is benzoyl halide and preferably benzoyl chloride. In a further embodiment the acylating agent is diterbutyl dicarbonate.

In one embodiment, there is provided a process comprising acylation of a compound of formula

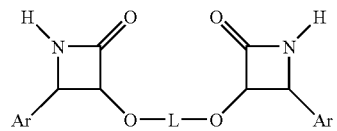

with benzoyl chloride or di-tert-butyldicarbonate, $(BOC)_2O$ to provide a compound of formula

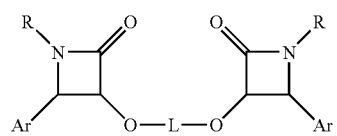

chiral or racemic, wherein Ar is an aryl group, R is acyl and L is a cleavable linker, chiral or non chiral, preferably selected from the group consisting of hydrolysable ketals, acetals, silyl, diesters, and hydrogenatable benzyl group.

With reference to scheme 1, compound of formula I, in accordance with the present invention, can be prepared as described from the compounds 5', 5" and 5''' together. More particularly, a linker "L" having two leaving groups such as an halogen or a group derived from a carboxylic acid group (e.g. acyl chloride, a carbodiimide derived group, a pyridinium group) is treated with a glycolate ester 2', in which Rb is a group such as an alkyloxy, to produce a compound 3' that is further treated with an aldimine 4' to produce a compound 5' or 5". Ra is a group susceptible to be cleaved in situ from the reaction condition or the isolation process (such as trimethyl silyl).

Alternatively, when Rb is a leaving group such as an halide (e.g. chloride) Ra is a group that is susceptible to be cleaved at a later stage for example by oxydative cleavage (e.g. 4-methoxyphenyl group). Compound 5" can be acylated to produce a compound 5''' in which R is an acyl group such as tert-butyloxycarbonyl or a benzoyl.

Scheme 1

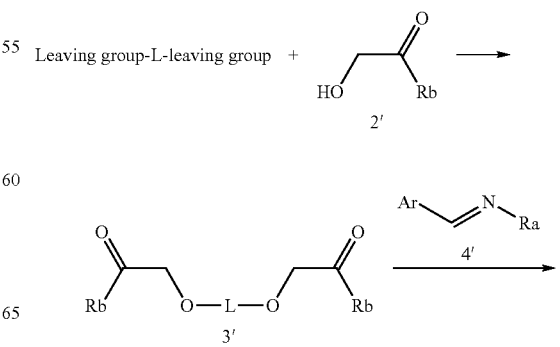

17

-continued

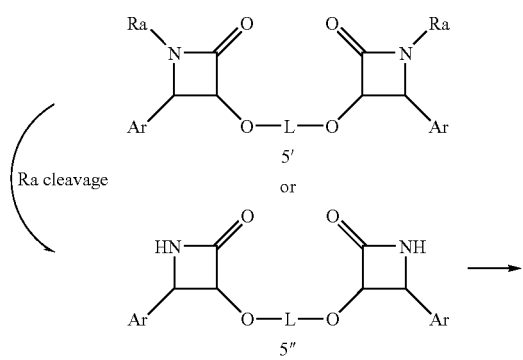

18

-continued

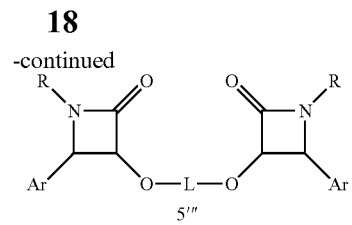

With reference to scheme 2, compounds of formulas III and IV are prepared from a chiral auxiliary such as the acetonide of optically pure tartaric acid, compound 1. Compound 1 is reacted with ethyl glycolate, 2 under coupling conditions to provide compound 3. Reacting compound 3 with aldimine 4 provides compound 5 in which diastereomeric excess is induced at the β-lactam chiral centers by the presence of the chiral tartrate group. Compound 5 is converted to a compound of formula III in the presence of benzoyl chloride or to a compound of formula IV in the presence of di-tert-butyldicarbonate.

Scheme 2

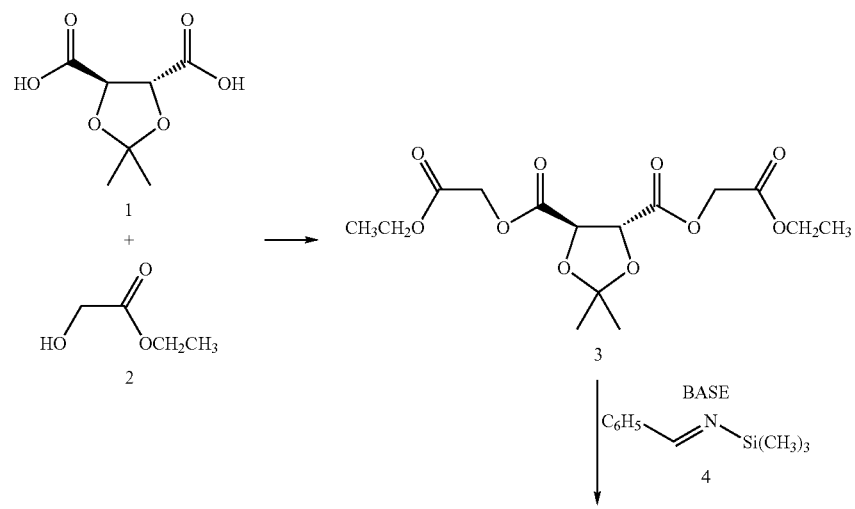

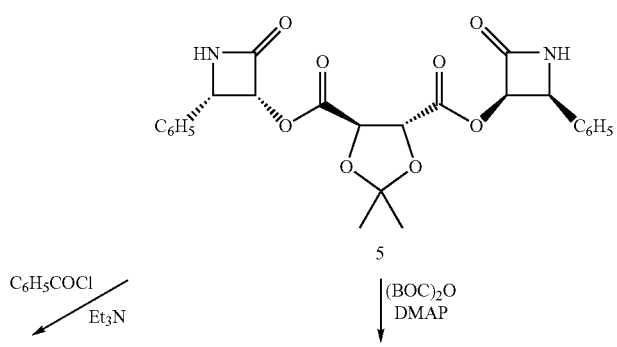

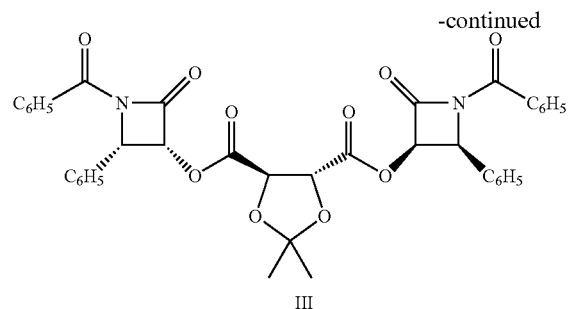

III

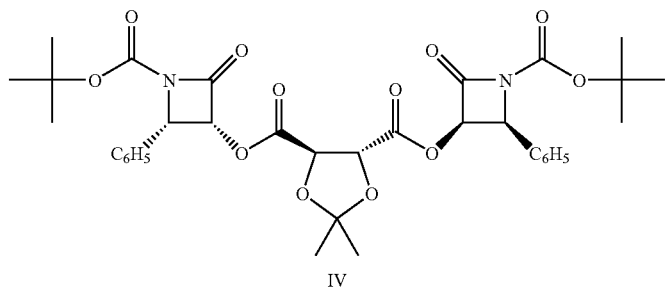

IV

With reference to scheme 3, compound of formula 5 (as described in scheme 2) can be prepared when compound 6 is reacted with aldimine compound 7, to provide compound 8 in which diastereomeric excess is again induced at the β-lactam chiral centers by the presence of the chiral tartrate group. Compound 8 is oxidized to compound 5 in the presence of an oxidizing agent such as the CAN reagent.

Scheme 3

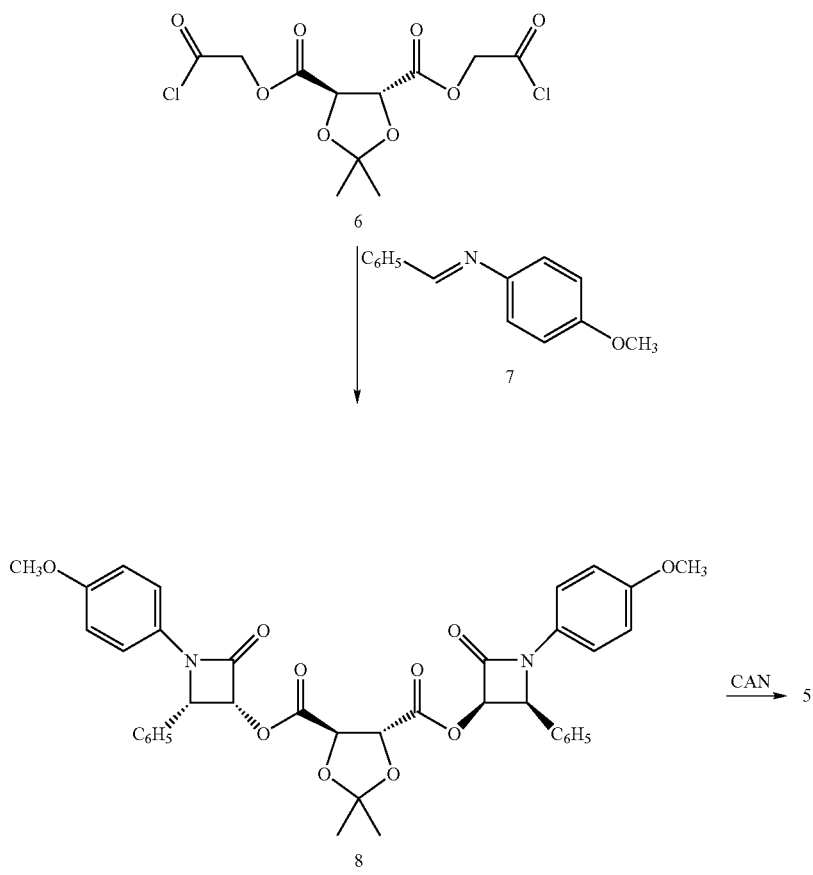

In one aspect, there is provided a process for producing a compound of formula VI

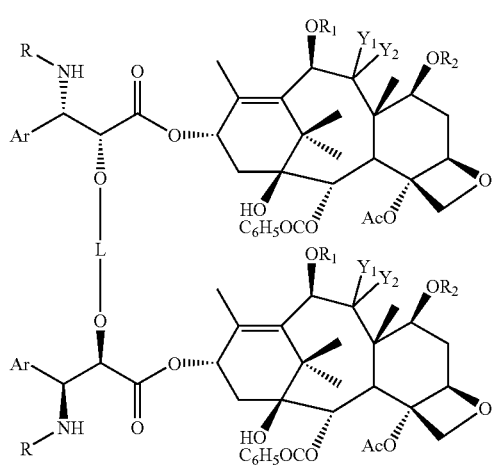

comprising treating a taxane precursor compound of formula

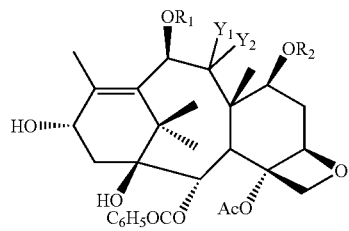

with a compound of formula

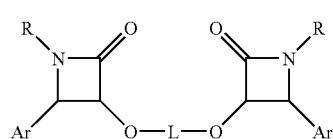

wherein R, $R_1$, $R_2$, $Y_1$, $Y_2$, Ar and L are as defined herein.

In one aspect the present invention provides a process for the preparation of paclitaxel, docetaxel, and analogs thereof where β-lactams of formula I:

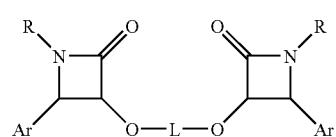

Further in accordance with the present invention, there is provided a method to use β-lactams of formula I for the preparation of paclitaxel, docetaxel and analogs thereof.

In one embodiment, the 13-hydroxy group of a suitably protected baccatin III compound is reacted with the β-lactam of formula I to provide a compound of formula II

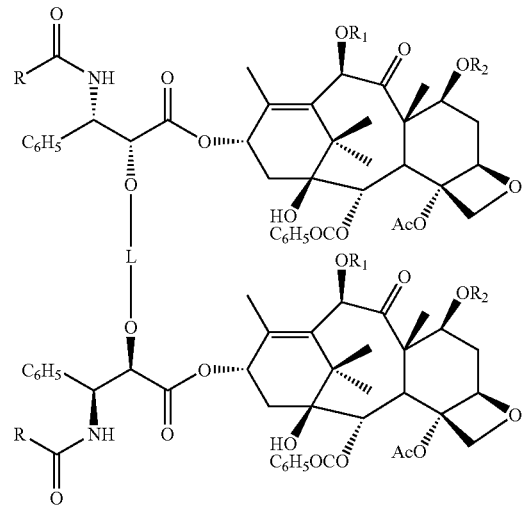

wherein R identical or different, are independently aryl, acyl or acyloxy, $R_1$, $R_2$, identical or different, are independently acyl, hydrogen or a hydroxy protecting group and L is a cleavable linker, and more preferably a chiral auxiliary (linker). The linker is then removed by hydrolysis or hydrogenation and protecting groups are removed to provide the require paclitaxel, docetaxel and analogs thereof.

In one embodiment of the invention, there is provided a process comprising reacting of a compound of formula

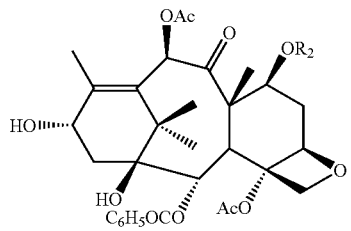

with a compound of formula

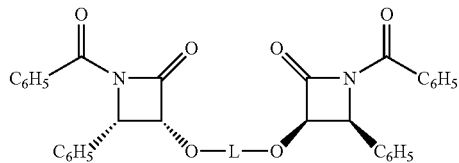

to provide a compound of formula

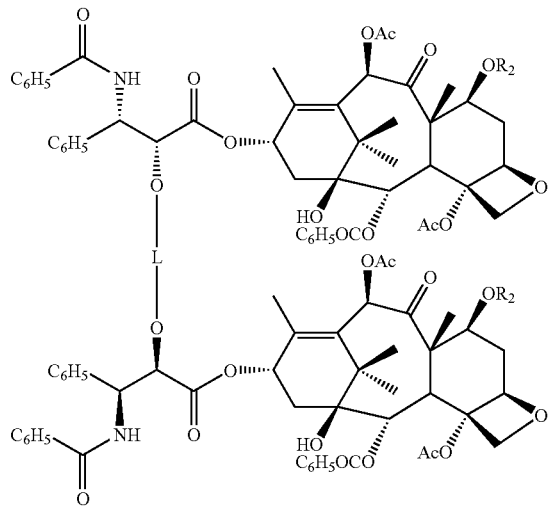

wherein $R_2$ is a hydroxy protecting group and L is a cleavable linker, chiral or non chiral, preferably selected from the group consisting of hydrolysable ketals, acetals, silyl, diesters, and hydrogenolizable benzyl group.

In one embodiment of the invention, there is provided a process comprising reacting of a compound of formula

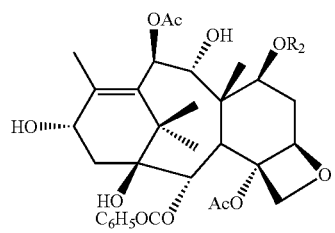

with a compound of formula

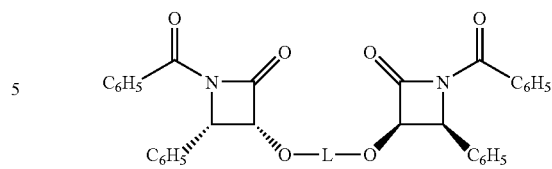

to provide a compound of formula

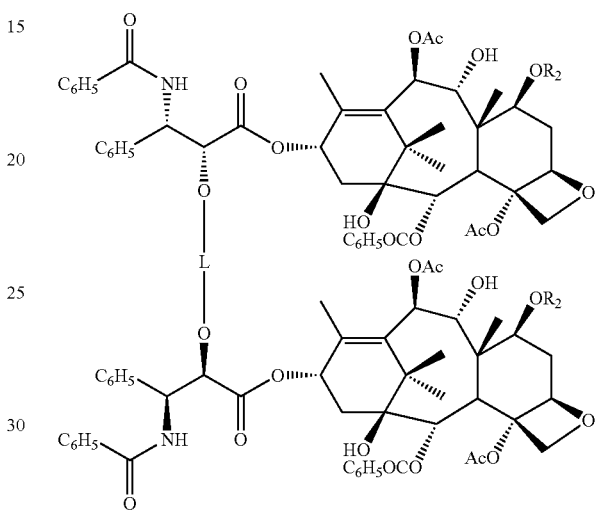

wherein $R_2$ is a hydroxy protecting group and L is a cleavable linker, chiral or non chiral, preferably selected from the group consisting of hydrolysable ketals, acetals, silyl, diesters, and hydrogenolizable benzyl group.

In a further embodiment, there is provided a process comprising reacting of a compound of formula

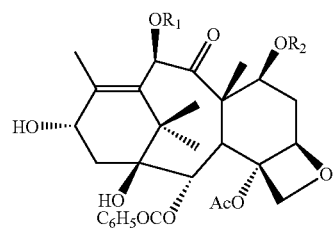

with a compound of formula

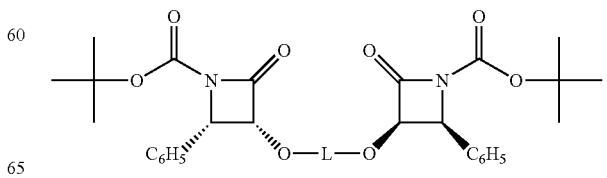

to provide a compound of formula

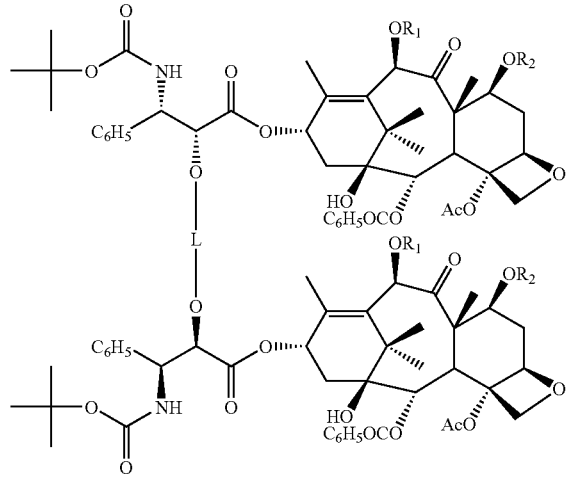

wherein $R_1$ and $R_2$ are a hydroxy protecting group and L is a cleavable linker, chiral or non chiral, preferably selected from the group consisting of hydrolysable ketals, acetals, silyl, diesters, and hydrogenolizable benzyl group.

In a further embodiment, there is provided a process comprising reacting a compound of formula with a compound of formula

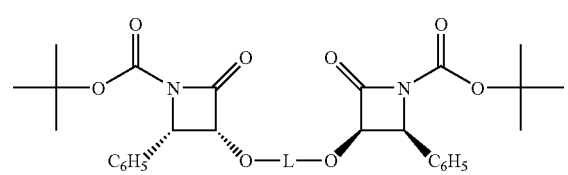

to provide a compound of formula

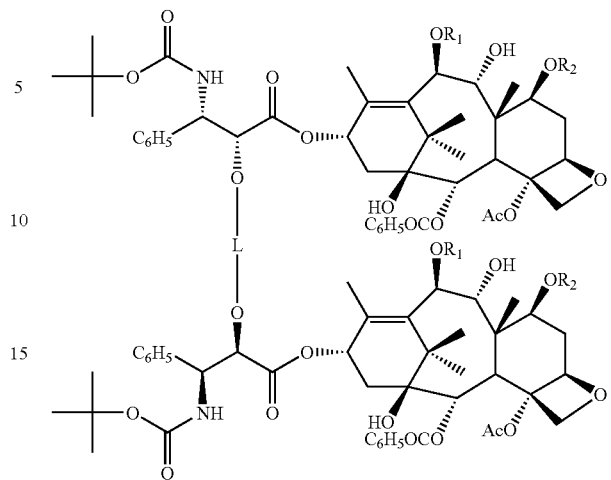

wherein $R_1$ and $R_2$ are a hydroxy protecting group and L is a cleavable linker, chiral or non chiral, preferably selected from the group consisting of hydrolysable ketals, acetals, silyl, diesters, and hydrogenolisable benzyl group.

Preferably, the hydroxy protecting group is selected from the group consisting of ethoxyethyl, triethylsilyl, triisopropylsilyl, t-butyldimethylsilyl, t-butyldiphenylsilyl, benzyl and tert-butyloxycarbonyl. More preferably, the hydroxy protecting group is triethylsilyl.

In a further aspect, there is provided a process for producing a compound of formula

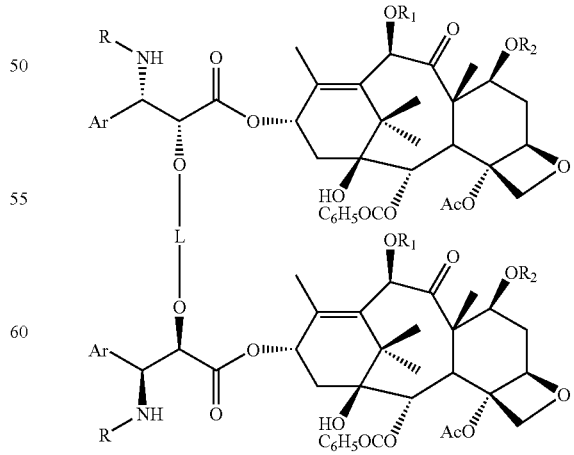

comprising treating a compound of formula

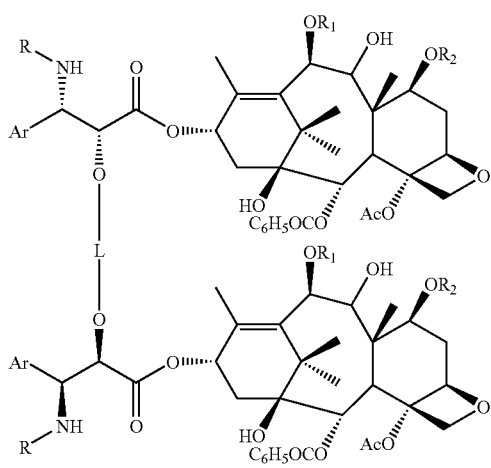

with an oxidizing agent; wherein R, $R_1$, $R_2$, Ar and L are as defined herein.

In one embodiment, there is provided a process comprising oxidation of a compound of formula

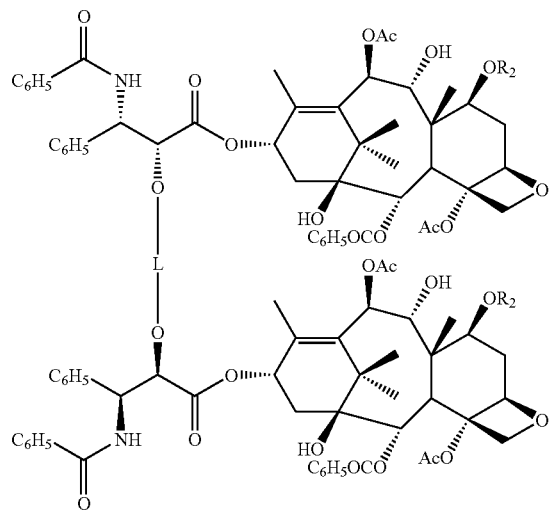

with an oxidizing agent to provide a compound of formula

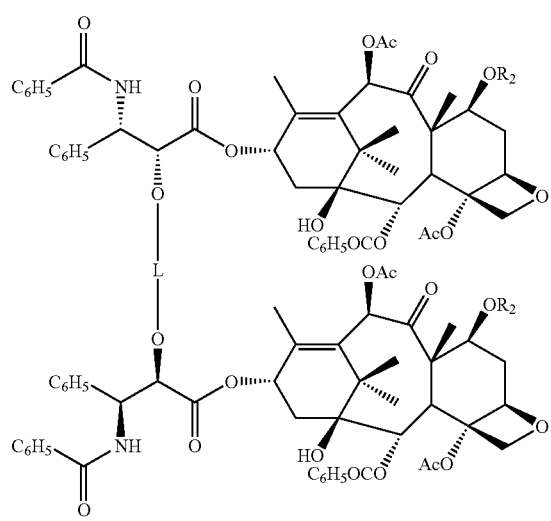

wherein $R_2$ is a hydroxy protecting group and L is a cleavable linker, chiral or non chiral, preferably selected from the group consisting of hydrolysable ketals, acetals, silyl, diesters, and hydrogenolyzable benzyl group.

In one embodiment, there is provided a process comprising oxidation of a compound of formula

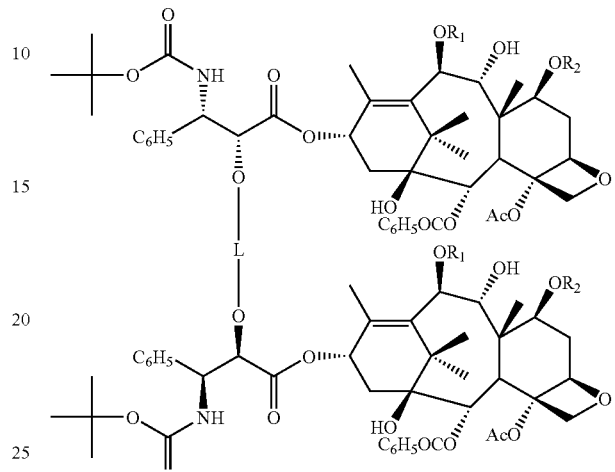

with an oxidizing agent to provide a compound of formula

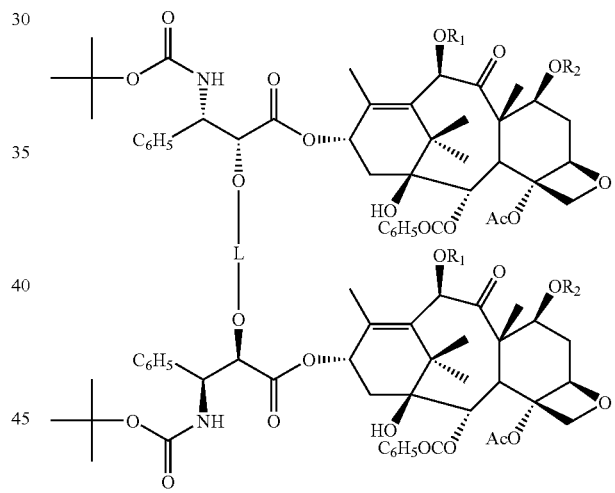

wherein $R_1$ and $R_2$ are a hydroxy protecting group and L is a cleavable linker, chiral or non chiral, preferably selected from the group consisting of hydrolysable ketals, acetals, silyl, diesters, and hydrogenolizable benzyl group.

In one embodiment, the oxidizing agent is selected from the group consisting of o-iodoxybenzoic acid (IBX), Dess-Martin periodinane, iodosobenzene, iodozobenzene diacetate, Jone's reagent, pyridinium dichromate, pyridinium chlorochromate, potassium permanganate and Swern reagent. Preferably, the oxidizing agent is Dess-Martin periodinane.

Preferably, hydroxy protecting group is selected from the group consisting of ethoxyethyl, triethylsilyl, triisopropylsilyl, t-butyldimethylsilyl, t-butyldiphenylsilyl, benzyl and tert-butyloxycarbonyl. More preferably, hydroxy protecting group is triethylsilyl.

In a further embodiment, L, $R_1$ and $R_2$ are as defined herein.

In accordance with one aspect of the invention, there is provided a process of preparing docetaxel comprising the reaction sequence

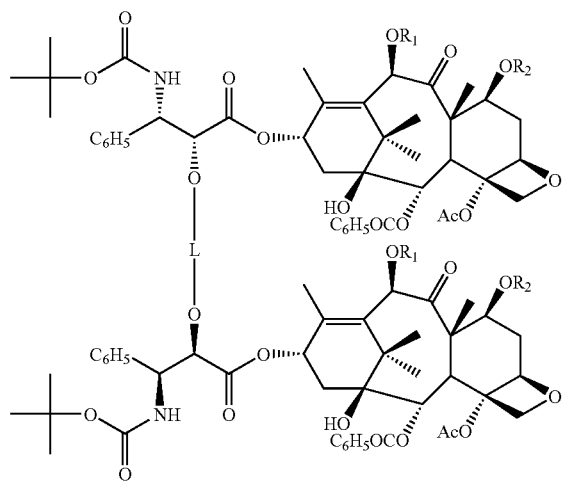
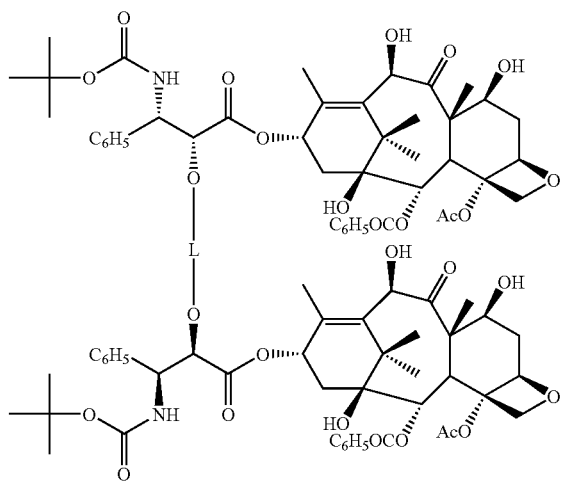

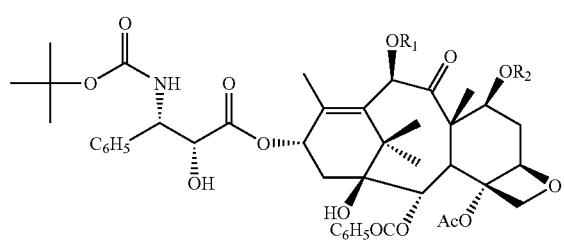
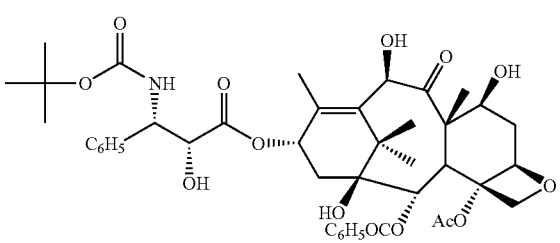

wherein L, $R_1$ and $R_2$ are as defined herein and said process comprising the steps of: a) cleaving the linker L releasing docetaxel protected at the 7 and 10-hydroxy positions and deprotecting the hydroxy groups at the 7 and 10-hydroxy positions to obtain docetaxel or b) deprotecting the hydroxy groups at the 7 and 10-hydroxy positions followed by the cleaving of the linker L releasing docetaxel.

In a further embodiment, docetaxel is obtained in the anhydrous form from crystallization in non protic solvents. In a further embodiment, docetaxel is obtained as the trihydrate form from crystallization in protic solvents.

In accordance with one aspect of the invention, there is provided a process of preparing paclitaxel comprising the reaction sequence

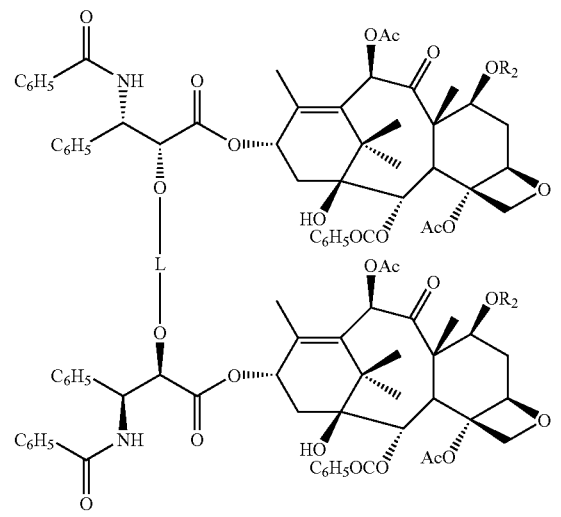
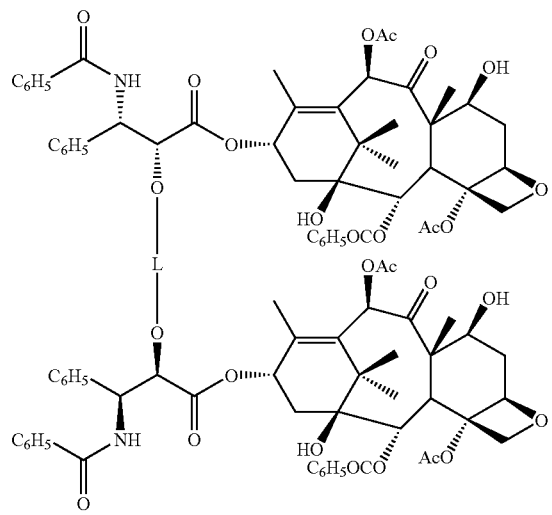

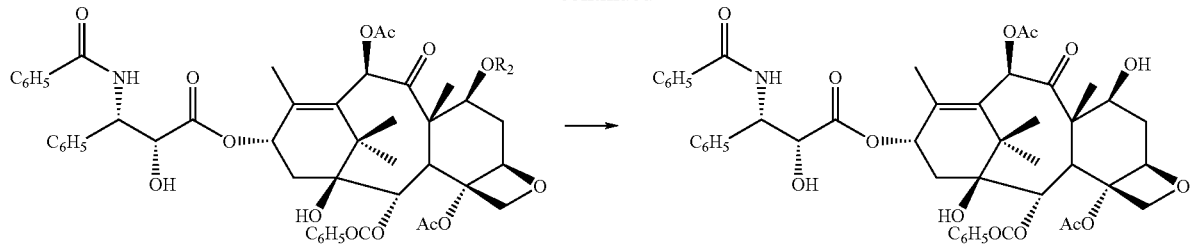

wherein L, and $R_2$ are as defined herein and said process comprising the steps of: a) cleaving the linker releasing paclitaxel protected at the 7-hydroxyl position and deprotecting the hydroxy groups at the 7-hydroxyl position to obtain paclitaxel or b) deprotecting the hydroxy groups at the 7-hydroxy positions and cleaving the linker L releasing paclitaxel.

In a further embodiment, paclitaxel is obtained in the anhydrous form from crystallization in non protic solvents. In a further embodiment, paclitaxel is obtained in the trihydrate form from crystallization in protic solvents.

With reference to scheme 4, paclitaxel is synthesized using a compound of formula III. Compound 9, obtained from naturally occurring 10-DAB as described in WO 2006/102758, is reacted with a compound of formula III in the presence of a base to provide compound 10. The compound 10 is then cleaved by hydrolysis in the presence of a mild base and the 7-hydroxy protecting group is removed with acid to provide paclitaxel.

Still with reference to scheme 4, in the synthesis of docetaxel compound 11, obtained from naturally occurring 10-DAB as described in WO 2006/102758, is reacted with a compound of formula IV in the presence of a base to provide compound 12. Removal of the linker L by hydrolysis in the presence of a mild base and removal of the hydroxy protecting groups at the 7 and 10 positions with mild acid provides docetaxel.

Scheme 4

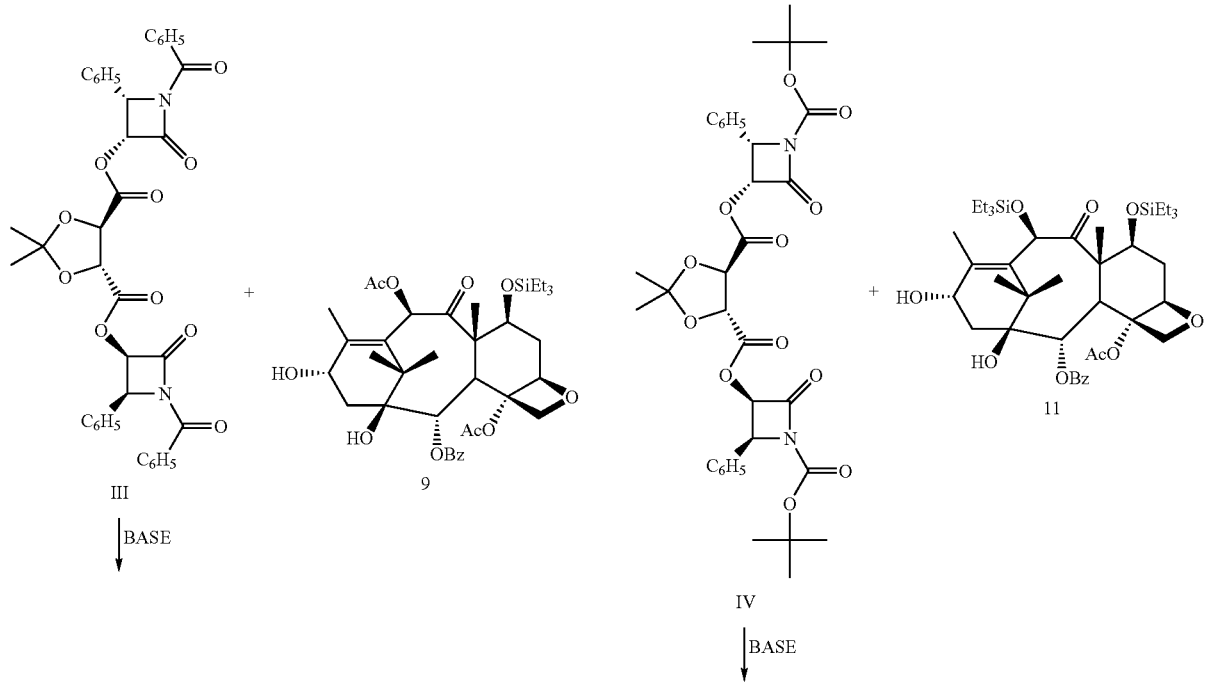

33
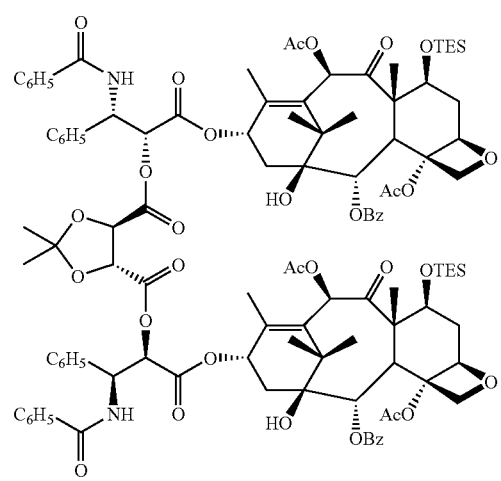
↓ 10
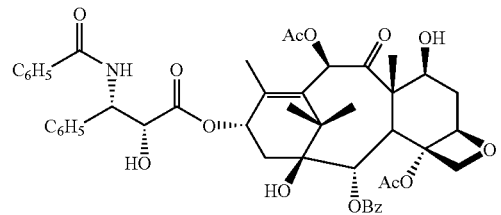
PACLITAXEL
34
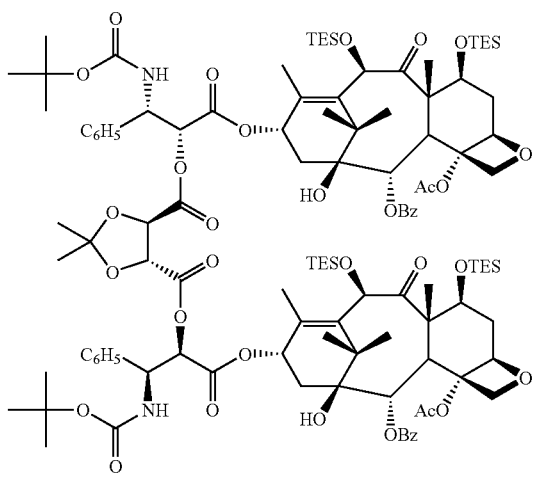
↓ 12
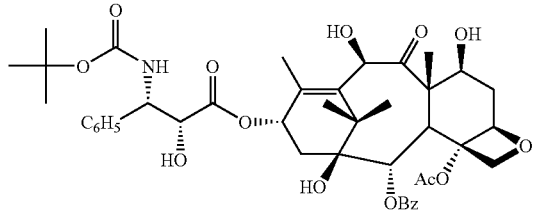
DOCETAXEL With reference to scheme 5, compound 13, is prepared from 9-DHAB III, a naturally occurring taxane found in the needles of the Canada yew as described in WO 2006/102758. Compound 13, is reacted with a compound of formula III in the presence of a base to provide compound 14. Oxidation of the 9-hydroxy groups of each of the two taxane moieties of compound 14 using an oxidizing agent provides compound 10 Compound 10, is then transformed to paclitaxel using successive treatment with mild base and mild acid.

with reference to scheme 5, compound 15 is prepared from naturally occurring 9-DHAB III as described in WO 2006/102758. Compound 15, is reacted with a compound of formula IV in the presence of a base such as to provide compound 16. Oxidation of the 9-hydroxy groups of each of the two taxane moieties of compound 16 using an oxidizing agent provides compound 12. The oxidized product, compound 12, is then transformed to docetaxel using successive treatment with mild base and mild acid.

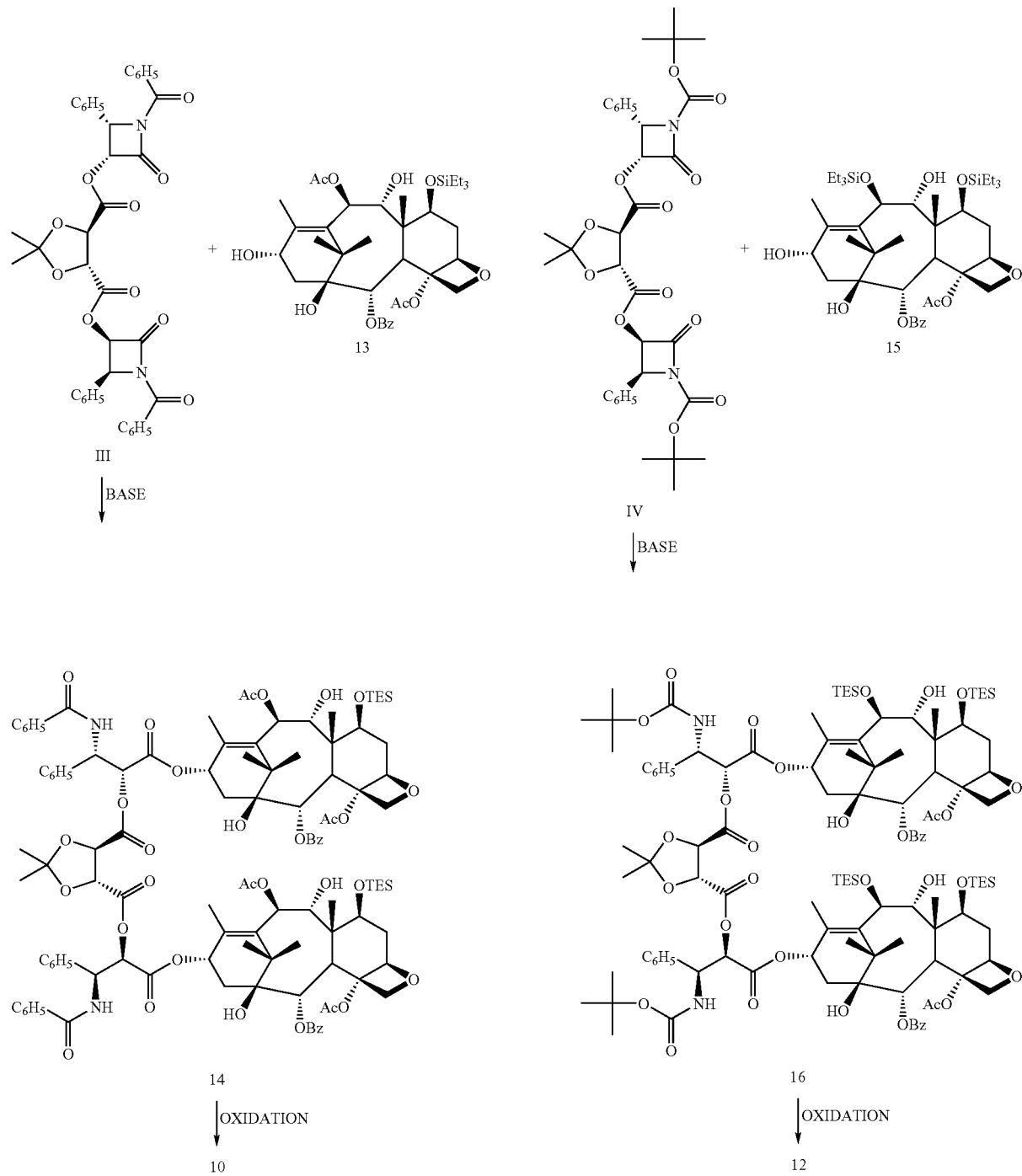

SCHEME 5

Compounds of formula I

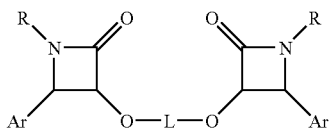

are prepared as described before using a compound of general formula 3'

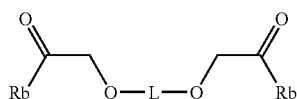

wherein Ar, R, Rb are as defined above. The linker L is as described herein and examples include ketal or acetal linker, silyl linker of formulas

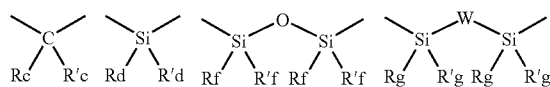

wherein Rc and R'c, Rd and R'd, Rf and R'f, Rg and R'g and W are as defined herein.

The compounds of formula 3' are typically prepared as described in scheme 1 using the appropriate linker L. The reagent "Leaving group-L-Leaving group" referred to in scheme 1 can be prepared in accordance with conditions known in the art.

For instance, when the linker is

a compound of general formula 2', wherein Rb is a group such as an alkyloxy, is treated with a ketone or aldehyde of formula Rc—C(O)—R'c (e.g. as acetone, acetaldehyde, cyclohexanone) under water removal conditions (e.g. azeotropic solvent or water trapping agent such as methylorthoformate) and a trace of an acid catalyst (e.g. PTSA).

When the linker is

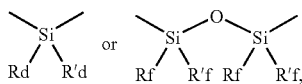

a compound of general formula 2', wherein Rb is a group such as an alkyloxy, is treated with a reagent having the general formula Rd—Si(leaving group)$_2$—R'd (e.g. (CH$_3$)$_2$SiCl$_2$) or RfR'f—Si(leaving group)-O—Si(leaving group)-RfR'f (e.g. (CH$_3$)$_2$ClSi—O—SiCl(CH$_3$)$_2$) under appropriate basic conditions.

When the linker is

a compound of general formula 2', wherein Rb is a group such as an alkyloxy, is treated with a reagent having the general formula RgR'g—Si(leaving group)-W—Si(leaving group)-RgR'g. An example wherein Rg and R'g are i-propyl, the leaving group is chloride and W is a methyl is

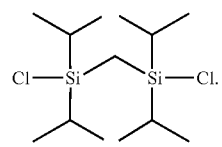

The linkers described above may be cleaved at a suitable stage of the process using standard conditions such as mild hydrolytic conditions, for example using a dilute inorganic acid solution such as HCl or a source of fluoride ions in case where a silicon based linker is used.

When the linker is —CH$_2$—(C$_6$H$_5$)—(CH$_2$)— a compound of general formula 2', wherein Rb is a group such as an alkyloxy, is treated with a reagent having the general formula (leaving group)-CH$_2$—(C$_6$H$_5$)—(CH$_2$)-(leaving group) such as Cl—CH$_2$—(C$_6$H$_5$)—(CH$_2$)—Cl.

The above-described linker having benzylic position may be cleaved at a suitable stage of the process using standard hydrogenolysis conditions such as hydrogen or a source of hydrogen (e.g. cyclohexanediene) and a suitable catalyst.

The present invention will be more readily understood by referring to the following examples which are given to illustrate the invention rather than to limit its scope.

Example 1

Preparation of Compound of Formula III

Compound 1 is reacted with two equivalents of ethyl glycolate, in the presence of 3.0 equivalents of dicyclohexylcarbodiimide (DCC) and a catalytic amount of dimethylaminopyridine (DMAP) in dichloromethane for 18 hours and purified on silica gel to provide compound 3. Reacting compound 3 with 2.2 equivalents each of aldimine 4 and LDA in THF at −10° C. for 18 hours provides compound 5. Compound 5 is converted to a compound of formula III in the presence of 3.0 equivalents of benzoyl chloride and 10 equivalents of triethylamine in dichloromethane.

Example 2

Preparation of Compound of Formula IV

Compound of formula IV is prepared as described in example 1, with the exception that compound 5 is treated in the presence of 3.0 equivalents of di-tert-butyldicarbonate in dichloromethane.

Example 3

Alternative Preparation of Compound of Formula 5

Compound 6 is reacted with 2.2 equivalents of p-methoxyaniline, aldimine compound 7, in dichloromethane to provide compound 8. Compound 8 is oxidized to compound 5 in the presence of 5.6 equivalents of ceric ammonium nitrate (CAN) reagent in acetonitrile and water (in a ratio of 1:1).

Example 4

Synthesis of Compound of Formula 10

Compound 9, obtained from naturally occurring 10-DAB, is reacted with a compound of formula III in the presence of lithium hexamethyldisilizide (LHMDS) in THF to provide compound 10.

Example 5

Synthesis of Paclitaxel

The linker in compound 10, as prepared in example 4, is cleaved by hydrolysis in the presence of 2 equivalents of sodium carbonate in 3.5 volume of methanol and the 7-hydroxy protecting group is removed with dilute (0.2M) methanolic hydrochloric acid to provide paclitaxel.

Example 6

Synthesis of Compound of Formula 12

Compound 11, obtained from naturally occurring 10-DAB, is reacted with 1.5 equivalents of a compound of formula IV in the presence of 3 equivalents of LHMDS in THF to provide compound 12.

Example 7

Synthesis of Compound of Formula 14

Compound 13 is reacted with 1.5 equivalents of a compound of formula III in the presence of 3 equivalents of lithium hexamethyldisilizide (LHMDS) in THF to provide compound 14.

Example 8

Alternative Synthesis of Compound of Formula 10

Oxidation of the 9-hydroxy groups of each of the two taxane moieties of compound 14, as provided in example 7, is carried out using the 3 equivalents of Dess-Martin periodinane for each equivalents of compound 14 in dichloromethane to provide compound 10.

Example 9

Alternative Synthesis of Compound of Formula 12

Compound 15 is reacted with 1.5 equivalents of a compound of formula IV in the presence of 3 equivalents of lithium hexamethyldisilizide (LHMDS) in THF to provide compound 16. Oxidation of the 9-hydroxy groups of each of the two taxane moieties of compound 16 using 3 equivalents of the Dess-Martin periodinane for each equivalents of compound 16 in dichloromethane provides compound 12.

Example 10

Synthesis of Docetaxel

Docetaxel is prepared from compound of formula 12 using conditions similar to what is described in example 5.

Example 11

Synthesis of Bis(diisopropylchlorosilyl)methane

Step 1: Synthesis of Bis(diisopropylsilyl)methane

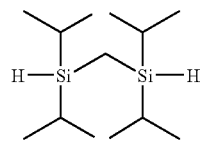

A solution of bis(dichlorosilyl)methane and $CuCl_2$ in THF was treated with isopropylmagnesium chloride, over 2 h. The product was extracted in Hexane, dried over $MgSO_4$ and distilled to obtain the Bis(diisopropylsilyl)methane in 78% yield.

Step 2: Synthesis of Bis(diisopropylchlorosilyl)methane

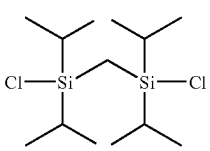

To a mixture of Bis(diisopropylsilyl)methane, from step 1, and $PdCl_2$ was added dry $CCl_4$ and kept the mixture at 60° C. over 2 h. Then it was filtered and distilled to obtain Bis (diisopropylchlorosilyl)methane in 87% yield. (see Ke Wen, Suetying Chow, Yogesh S. Sanghvi, and Emmanuel A. Theodorakis, J. Org. Chem. Vol. 67, No. 22, 2002).

Example 12

Synthesis of Bis(diisopropyl-9-Dihydro-7,10-bis-triethylsilyl-10-deacetyl-baccatin-III-silyl)methane

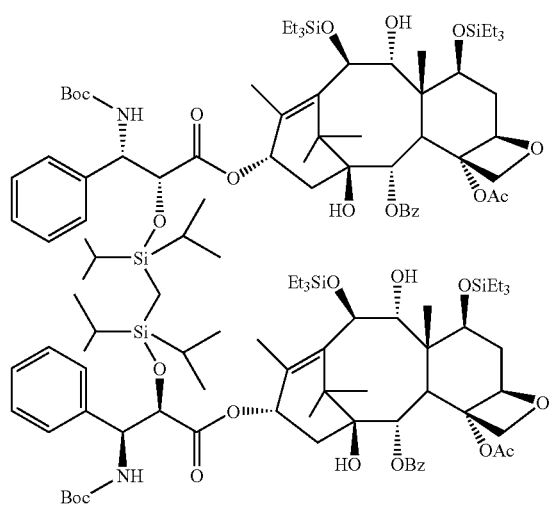

The bis protected taxane

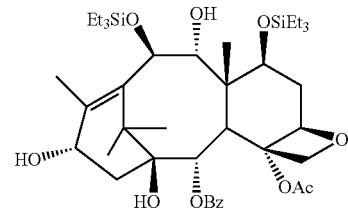

(200 mg, 0.26 mmol) was solubilized in 2 ml of THF. The solution was cooled to −45° C. and 1.0 M LiHMDS was added (258 ul, 0.26 mmol) under an atmosphere of argon and left stirring over 15 min. Then was added the reagent

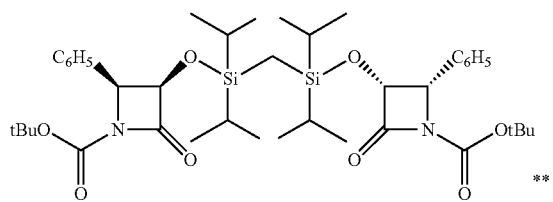

(99 mg, 0.13 mmol) in 2 ml of THF and left stirring over 2 h at −45° C., and at −25° C. overnight. The solution was quenched with sat. NH4Cl (15 ml) and extracted with (EtOAc×3×25 ml). The organic phase was washed with brine (2×20 ml), dried over sodium sulfate, taken to dryness, passed over silica gel, (EtOAc/Hexane 10%-25%) to obtain 245 mg of the dimer in 82% yield. 1H NMR (Acetone-d6, 600 MHz) δ 8.01-7.45, (20H, o-Bz and Ph); 6.07 (t; 2H, J=8.6 Hz; H13); 5.93 (br, d; 2H, J=8.9 Hz; NH41); 5.81 (br.d; 2H, J=5.3 Hz; H2); 5.25 (br, d; 2H, J=9.4 Hz; H31); 5.03 (d; 2H, J=9.4 Hz; OH9); 4.91 (d; 2H, J=9.4 Hz; H5); 4.87 (br, d; 2H, J=9.4 Hz; H21); 4.84 (d; 2H, J=9.4 Hz; H10); 4.58 (dd; 2H, J=9.9, 7.1 Hz; H7); 4.18 (o; 2H, H9); 4.18 (o; 2H, H20a); 4.15 (d; 2H, J=8.1 Hz; H20b); 3.62 (s; 2H, OH1); 3.14 (d; 2H, J=5.5 Hz; H3); 2.57 (o, 2H, 6Ha); 2.55 (o.s; 6H, OAc); 2.42 (br; 2H, H14a); 2.27 (br, 2H, H14b); 1.92 (m; 2H, H6b); 1.86 (br, s; 6H, Me18); 1.82 (s; 6H, Me19); 1.74 (s, 6H, Me17); 1.37 (s; 18H, tBu-CO-Me18); 1.32 (s, 6H, Me16); 1.07 (o.t; 6H, Si7-CH2-Me); 1.01 (o.t; 6H, Si10-CH2-Me); 1.05-0.85 (m; 2H, Si—CH(Me)$_2$); 0.79 (q; 4H, Si7-CH2-Me); 0.69 (m; 4H, Si10-CH2-Me); −0.14 (s; 2H, Si—CH$_2$—Si).

Characterisation of the bis-Lactam reagent: Rf value of 0.3 on the TLC (Hexane/Acetone 30%). 1H NMR (Acetone-d6, 600 MHz) δ 7.36 (o; 4H, Ph-3m); 7.30 (o; 4H, Ph-3o); 7.30 (t; 2H, Ph-3p); 5.29 (d; 2H, J=5.9 Hz; H2); 5.15 (d; 2H, J=6 Hz; H3); 1.35 (s; 18H, C—O-Me3); 0.86-0.80 (o.d; 24H, Me2); 0.64 (septet; 2H, J=7.4 Hz; Si—CH); −0.18 (s, 2H, Si—CH2—Si).

Example 13

Synthesis of Bis(diisopropyl-7,10-bis-triethyisilyl-10-deacetyl-baccatin-III-silyl)methane

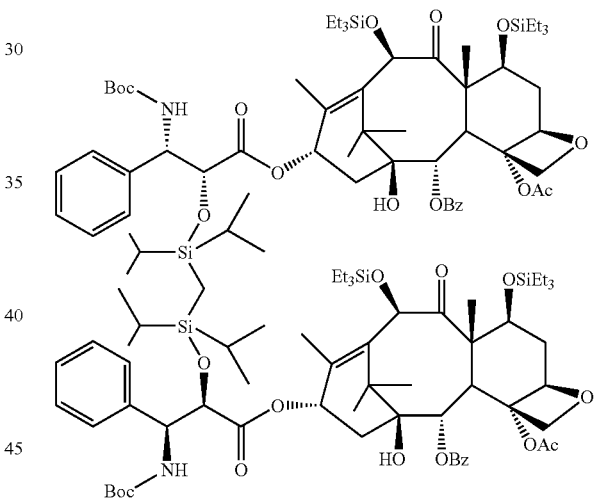

To the Dess-Martin periodinane (110 mg, 0.26 mmol) in 6 ml of dichloromethane was added 250 ul of pyridine. A solution of 200 mg (0.086 mmol) of the compound from example 12 in 4 ml of CH$_2$Cl$_2$ was added to the periodinane solution and left it standing over 18 h at room temperature. Saturated sodium bisulfite solution (5 ml) was added and the solution was extracted with ethyl acetate (3×30 ml). The organic phase was washed with brine (2×20 ml), then with water (2×20 ml), dried over sodium sulfate and evaporated to afford 178 mg of oxidized product in 89% yield. $^1$H NMR (Acetone-d6, 300 MHz) δ 8.62 (br.d; 2H, J=8.9 Hz; NH41); 8.12, (m; 4H, o-Bz); 7.75-7.28 (m; 16H, O-Bz and Ph); 6.19 (t; 2H, J=8 Hz; H13); 5.68 (d, 2H, J=7 Hz; H2); 5.40 (br, d; 2H, J=8 Hz; H31); 5.32 (b.s; 2H, 10H); 5.16 (s; 2H, H10); 4.92 (d; 2H, J=8 Hz; H5); 4.73 (s; 2H, H21); 4.41 (dd; 2H, J=10 Hz, 7 Hz; H7); 4.30 (d; 2H, J=8; H20b); 4.18 (dd; 2H, J=8 Hz, H20a); 4.18 (o; 2H, H20a); 3.86 (d; 2H, J=7 Hz; H3); 2.52 (s; 6H, OAc); 2.52 (o; 2H, H6a); 2.40-2.15 (m; 4H, H14a and H14b); 1.93 (o; 2H, H6b); 1.89 (s; 6H, Me18); 1.69 (s; 6H, Me19); 1.32 (s;

18H, tBu-C-Me3); 1.24 (s, 12H, Me16 and Me17); 1.04-0.56 (m; 88H, —SiEt3, Si—CH(CH3)2, Si—CH(CH3)2); −0.42 (s; 2H, Si—CH2—Si).

Example 14

Synthesis of Docetaxel

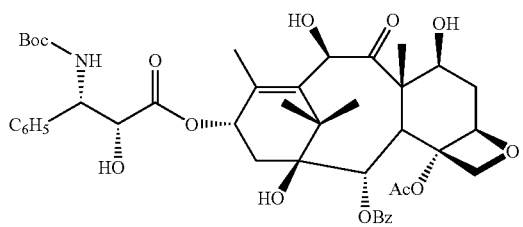

The starting material from example 13 (150 mg, 0.065 mmol) was dissolved in 20 ml of acetonitrile. A 0.2 M HCl solution (6 ml) was added and the solution was stirred at room temperature for 3 h. The pH of the solution was raised to 5.5 with aqueous sodium bicarbonate. Most of the acetonitrile was evaporated and ethyl acetate (50 ml) and water (50 ml) were added. The solution was extracted with ethyl acetate (3×50 ml). The organic phase was washed with water (2×50 ml), dried over sodium sulfate and evaporated. The product was purified on silica gel eluting with Acetone/Hexane (0-40%) to afford 94 mg of Docetaxel in 90% yield.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of formula

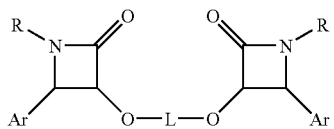

in racemic or in either isomerically pure form, wherein R is hydrogen, aryl or acyl, Ar is aryl, and L is a cleavable linker, chiral or non chiral.

2. A compound according to claim 1 wherein R is hydrogen.

3. A compound according to claim 1 wherein R is p-methoxyphenyl.

4. A compound according to claim 1 wherein R is benzoyl.

5. A compound according to claim 1 wherein R is tert-butyloxycarbonyl.

6. A compound according to claim 1 wherein L is a chiral tartaric diester acetonide having enantiomerically enriched or substantially pure (R,R) or (S,S) stereochemistry, or a mixture of (R,R) and (S,S) enantiomers including racemic mixtures.

7. A compound according to claim 1 wherein L is a chiral trans-1,2-cyclohexane di(carboxylate ester) having enantiomerically enriched or substantially pure (R,R) or (S,S) stereochemistry or a mixture of (R,R) and (S,S) enantiomers including racemic mixtures.

8. A compound according to claim 1 wherein L is a chiral 1,1'-binaphthyl-2,2'-di(carboxylate ester) having enantiomerically enriched or substantially pure (R) or (S) stereochemistry or a mixture of (R) and (S) enantiomers including racemic mixtures.

9. A compound according to claim 1 wherein L is of formula

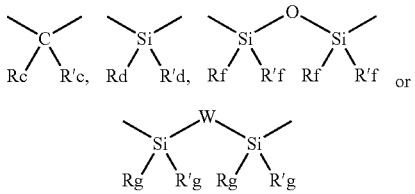

wherein Rc and R'c, identical or different are alkyl, aryl or hydrogen, Rd and R'd, identical or different are alkyl, aryl or hydrogen, Rf and R'f, identical or different are alkyl, aryl or hydrogen, Rg and R'g, identical or different are alkyl, aryl or hydrogen; W is an alkyl.

10. A compound according to claim 1 wherein L is —CH$_2$—(C$_6$H$_5$)—(CH$_2$)—.

11. A compound as defined in claim 1, wherein Ar is phenyl optionally substituted with one or more substituents.

12. A compound as defined in claim 1, wherein Ar is unsubstituted phenyl.

13. A compound of formula

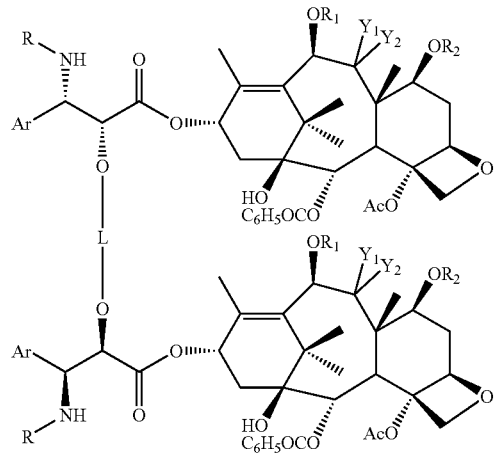

wherein Ar is an aryl, R is an acyl, preferably an aroyl or alkyloxycarbonyl, R$_1$, and R$_2$, identical or different, are independently acyl, hydrogen or a hydroxy protecting group, L is a cleavable linker, Y$_1$ is hydrogen, a hydroxy or a protected hydroxy group, Y₂ is a hydrogen or a protected hydroxy group or Y₁ and Y₂ taken together form a carbonyl group,
wherein L is of formula

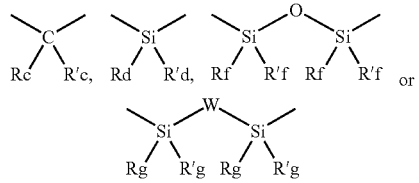

wherein Rc and R'c, identical or different are alkyl, aryl or hydrogen, Rd and R'd, identical or different are alkyl, aryl or hydrogen, Rf and R'f, identical or different are alkyl, aryl or hydrogen, Rg and R'g, identical or different are alkyl, aryl or hydrogen; W is an alkyl.

14. A compound as defined in claim 13, wherein Ar is phenyl optionally substituted with one or more substituents.

15. A compound as defined in claim 13, wherein Ar is unsubstituted phenyl.

16. A compound as defined in claim 13, wherein Y₁ is a hydroxyl and Y₂ is a hydrogen.

17. A compound as defined in claim 16, wherein Y₁ is a hydroxyl having stereochemistry

18. A compound as defined in claim 13, wherein Y₁ and Y₂ taken together form a carbonyl group.

19. A compound according to claim 13 wherein R is benzoyl, R₁ is acetyl and R₂ is a hydroxy protecting group.

20. A compound of formula

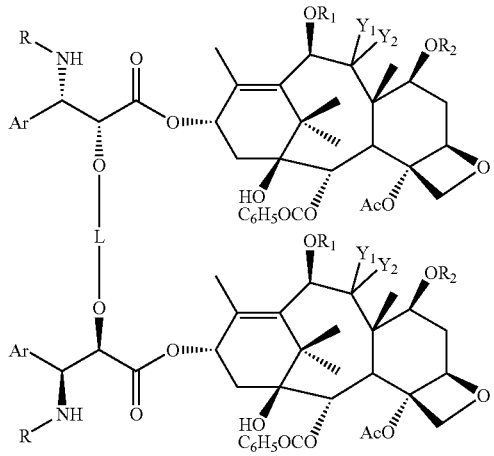

wherein Ar is an aryl, R is an acyl, preferably an aroyl or alkyloxycarbonyl, R₁, and R₂, identical or different are independently acyl, hydrogen or a hydroxy protecting group, L is a cleavable linker, Y₁ is hydrogen, a hydroxy or a protected hydroxy group, Y₂ is a hydrogen or a protected hydroxy group or Y₁ and Y₂ taken together form a carbonyl group,
wherein R is benzoyl, R₁ is acetyl and R₂ is selected from the group consisting of ethoxyethyl, triethylsilyl, triisopropylsilyl, t-butyldimethylsilyl, t-butyldiphenylsilyl, benzyl and tert-butyloxycarbonyl.

21. A compound according to claim 13 wherein R is benzoyl, R₁ is acetyl and R₂ is a hydrogen.

22. A compound of formula

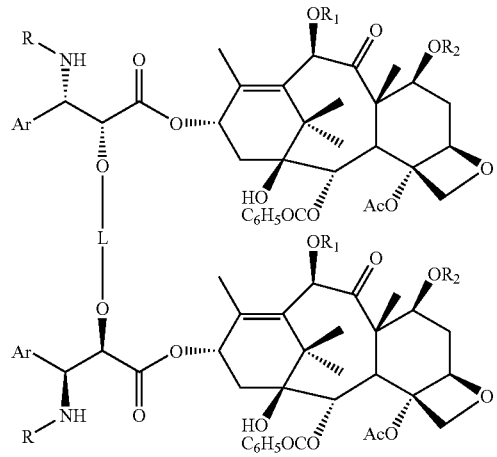

wherein Ar is an aryl, R is an acyl, preferably an aroyl or alkyloxycarbonyl, R₁, and R₂, identical or different are independently acyl, hydrogen or a hydroxy protecting group, L is a cleavable linker, Y₁ is hydrogen, a hydroxy or a protected hydroxy group, Y₂ is a hydrogen or a protected hydroxy group or Y₁ and Y₂ taken together form a carbonyl group,
wherein R is benzoyl and wherein R₁ and R₂ are both hydrogen.

23. A compound of formula

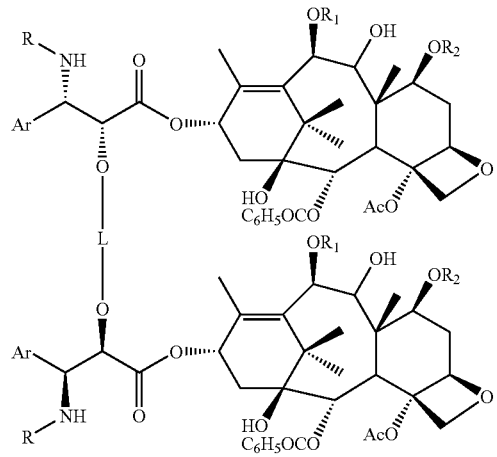

wherein Ar is an aryl, R is an acyl, preferably an aroyl or alkyloxycarbonyl, R₁, and R₂, identical or different are independently acyl, hydrogen or a hydroxy protecting group, L is a cleavable linker, Y₁ is hydrogen, a hydroxy or a protected hydroxy group, Y₂ is a hydrogen or a protected hydroxy group or Y₁ and Y₂ taken together form a carbonyl group,
wherein R is benzoyl and wherein R₁ and R₂ are both a hydroxy protecting group.

24. A compound according to claim 23 wherein R₁ and R₂ are selected from the group consisting of ethoxyethyl, triethylsilyl, triisopropylsilyl, t-butyldimethylsilyl, t-butyldiphenylsilyl, benzyl and tert-butyloxycarbonyl.

25. A compound of formula

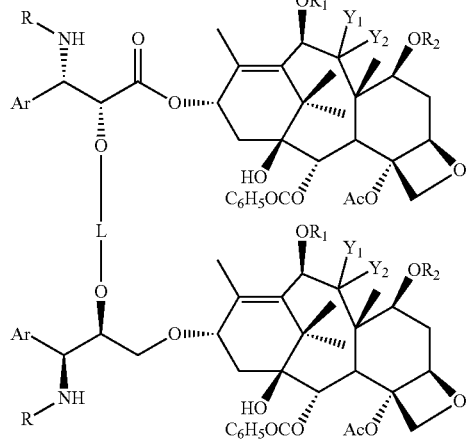

wherein Ar is an aryl, R is an acyl, preferably an aroyl or alkyloxycarbonyl, $R_1$, and $R_2$, identical or different are independently acyl, hydrogen or a hydroxy protecting group, L is a cleavable linker, $Y_1$ is hydrogen, a hydroxy or a protected hydroxy group, $Y_2$ is a hydrogen or a protected hydroxy group or $Y_1$ and $Y_2$ taken together form a carbonyl group, wherein R is tert-butyloxycarbonyl, $R_1$ is acetyl and $R_2$ is a hydroxy protecting group.

26. A compound according to claim 25 wherein $R_2$ is selected from the group consisting of ethoxyethyl, triethylsilyl, triisopropylsilyl, t-butyldimethylsilyl, t-butyldiphenylsilyl, benzyl and tert-butyloxycarbonyl and R is phenyl or tert-butoxy.

27. A compound of formula

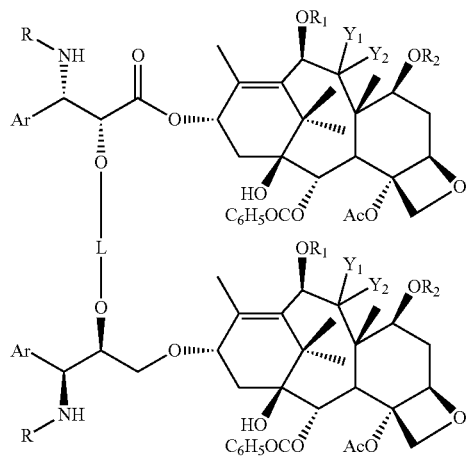

wherein Ar is an aryl, R is an acyl, preferably an aroyl or alkyloxycarbonyl, $R_1$, and $R_2$, identical or different are independently acyl, hydrogen or a hydroxy protecting group, L is a linker, $Y_1$ is en a hydroxy or a protected hydroxy group, $Y_2$ is a hydrogen or a protected hydroxy group or $Y_1$ and $Y_2$ taken together form a carbonyl group, wherein R is tert-butyloxycarbonyl, $R_1$ is acetyl and $R_2$ is a hydrogen.

28. A compound of formula

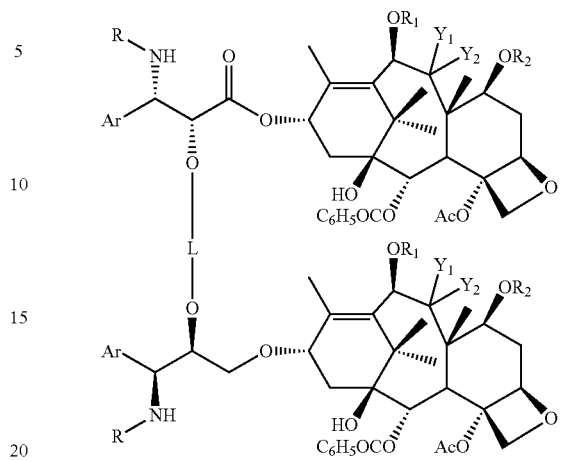

wherein Ar is an aryl, R is an acyl, preferably an aroyl or alkyloxycarbonyl, $R_1$, and $R_2$, identical or different are independently acyl, hydrogen or a hydroxy protecting group, L is a cleavable linker, $Y_1$ is hydrogen, a hydroxy or a protected hydroxy group, $Y_2$ is a hydrogen or a protected hydroxy group or $Y_1$ and $Y_2$ taken together form a carbonyl group, wherein R is tert-butyloxycarbonyl and wherein $R_1$ and $R_2$ are both hydrogen.

29. A compound of formula

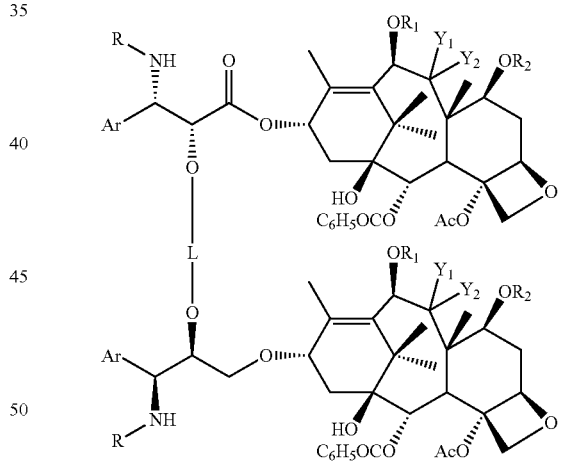

wherein Ar is an aryl, R is an acyl, preferably an aroyl or alkyloxycarbonyl, $R_1$, and $R_2$, identical or different are independently acyl, hydrogen or a hydroxy protecting group, L is a cleavable linker, $Y_1$ is hydroxy or a protected hydroxy group, $Y_2$ is a hydrogen or a protected hydroxy group or $Y_1$ and $Y_2$ taken together form a carbonyl group, wherein R is tert-butyloxycarbonyl and wherein $R_1$ and $R_2$ are both a hydroxy protecting group.

30. A compound according to claim 29 wherein $R_1$ and $R_2$ are selected from the group consisting of ethoxyethyl, triethylsilyl, triisopropylsilyl, t-butyldimethylsilyl, t-butyldiphenylsilyl, benzyl and tert-butyloxycarbonyl.

31. A compound of formula

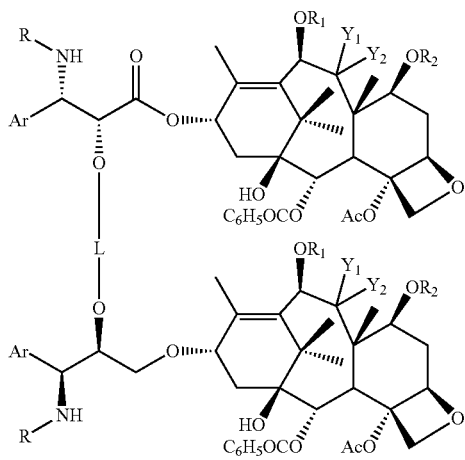

wherein Ar is an aryl, R is an acyl, preferably an aroyl or alkyloxycarbonyl, $R_1$, and $R_2$, identical or different are independently acyl, hydrogen or a hydroxy protecting group, L is a linker, $Y_1$ is en a hydroxy or a protected hydroxy group, $Y_2$ is a hydrogen or a protected hydroxy group or $Y_1$ and $Y_2$ taken together form a carbonyl group, wherein L is a chiral tartaric diester acetonide having enantiomerically enriched or substantially pure (R,R) or (S,S) stereochemistry, or a mixture of (R,R) and (S,S) enantiomers including racemic mixtures.

32. A compound of formula

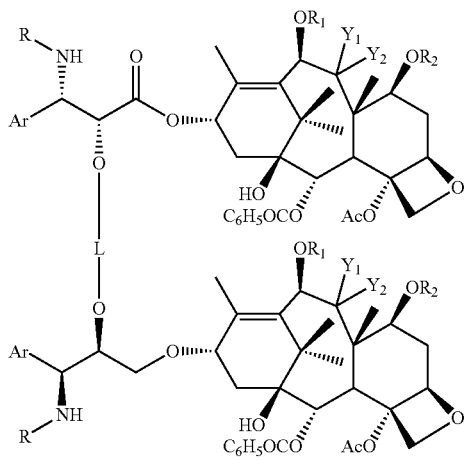

wherein Ar an aryl, R is an acyl, preferably an aroyl or alkyloxycarbonyl, $R_1$, and $R_2$, identical or different are independently acyl, hydrogen or a hydroxy protecting group, L is a cleavable linker, $Y_1$ is en a hydroxy or a protected hydroxy group, $Y_2$ is a hydrogen or a protected hydroxy group or $Y_1$ and $Y_2$ taken together form a carbonyl group, wherein L is a chiral trans-1,2-cyclohexane di(carboxylate ester) having enantiomerically enriched or substantially pure (R,R) or (S,S) stereochemistry or a mixture of (R,R) and (S,S) enantiomers including racemic mixtures.

33. A compound of formula

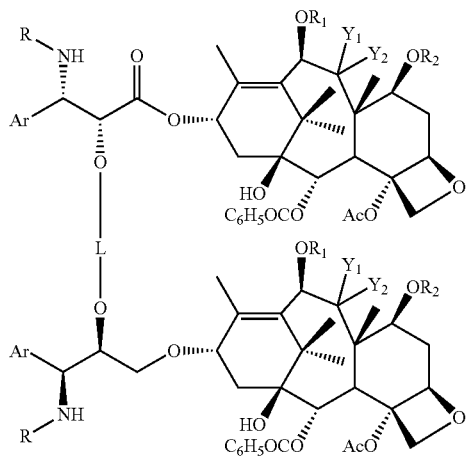

wherein Ar is an aryl, R is an acyl, preferably an aroyl or alkyloxycarbonyl, $R_1$, and $R_2$, identical or different are independently acyl, hydrogen or a hydroxy protecting group, L is a cleavable linker, $Y_1$ is hydrogen, a hydroxy or a protected hydroxy group, $Y_2$ is a hydrogen or a protected hydroxy group or $Y_1$ and $Y_2$ taken together form a carbonyl group, wherein L is a chiral 1,1'-binaphthyl-2,2'-di(carboxylate ester) having enantiomerically enriched or substantially pure (R) or (S) stereochemistry or a mixture of (R) and (S) enantiomers including racemic mixtures.

34. A compound of formula

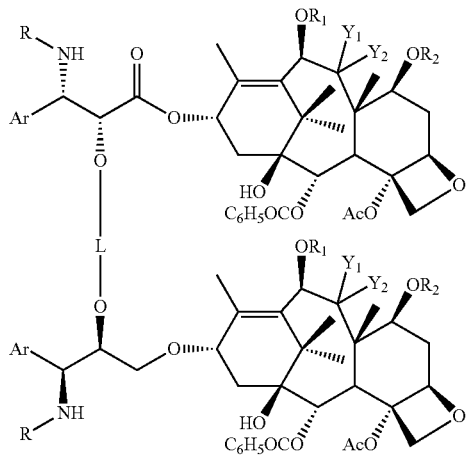

wherein Ar is an aryl, R is an acyl, preferably an aroyl or alkyloxycarbonyl, $R_1$, and $R_2$, identical or different are independently acyl, hydrogen or a hydroxy protecting group, L is a linker, $Y_1$ is en a hydroxy or a protected hydroxy group, $Y_2$ is a hydrogen or a protected hydroxy group or $Y_1$ and $Y_2$ taken together form a carbonyl group, wherein L is $-CH_2 13 (C_6H_5)-(CH_2)-$.

35. A process for producing a compound of formula 5''':

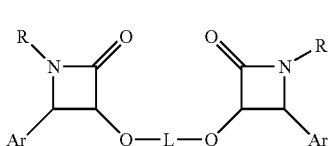

5''' wherein Ar is an aryl group and L is a cleavable linker, chiral or non chiral, R is an acyl group; comprising preparing a compound of formula 3':

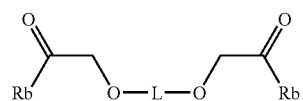

3' wherein L is as defined previously and Rb is an alkoxy group; and reacting said compound of formula 3' with a compound of formula:

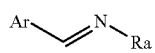

wherein Ar is as defined previously and Ra is a group cleaveable in situ from the reaction condition or from an isolation process; to produce a compound of formula 5''': wherein Ar and L are as defined previously:

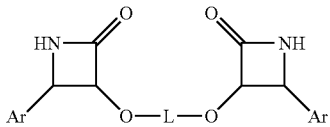

5''' wherein Ar and L are as described above,
or
preparing a compound of formula 3':

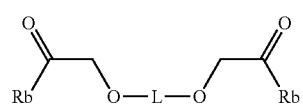

3' wherein L is as defined previously and Rb is a leaving group; and reacting said compound of formula 3' with a compound of formula:

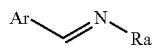

wherein Ar is as defined previously and Ra is a group cleavable under oxidative condition; to produce a compound of formula 5':

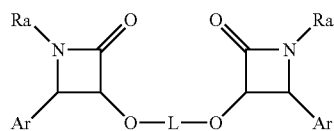

5' wherein Ar, Ra and L are as defined previously; and reacting said compound of formula 5' with an oxidizing agent to produce a compound of formula 5''

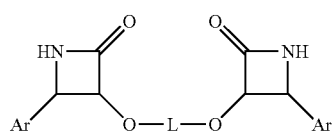

5'' wherein Ar and L are as described above;
and reacting said compound of formula 5'' with an acylating agent to produce said compound of formula 5'''.

36. A process according to claim 35 wherein R is benzoyl or tert-butyloxycarbonyl.

37. A process for producing a compound of formula

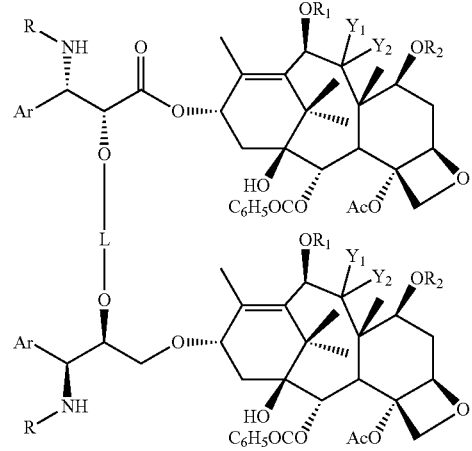

comprising treating a taxane precursor compound of formula

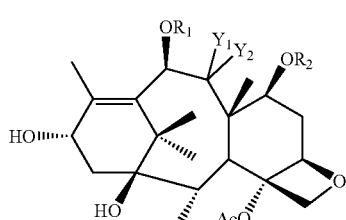

with a compound of formula

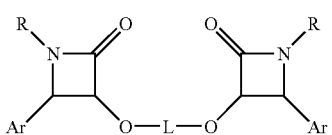

wherein Ar is an aryl, R is an acyl, $R_1$, and $R_2$, identical or different, are independently acyl, hydrogen or a hydroxy protecting group, L is a cleavable linker, $Y_1$ is hydrogen, a hydroxy or a protected hydroxy group, $Y_2$ is a hydrogen or a protected hydroxy group or $Y_1$ and $Y_2$ taken together form a carbonyl group.

38. A process according to claim 37, wherein R is an acyl that is an aroyl or alkyloxycarbonyl.

39. A process according to claim 37, wherein Ar is phenyl optionally substituted with one or more substituents.

40. A process according to claim 37, wherein Ar is unsubstituted phenyl.

41. A process according to claim 37, wherein $Y_1$ is a hydroxyl and $Y_2$ is a hydrogen.

42. A process according to claim 41, wherein $Y_1$ is a hydroxyl having stereochemistry

43. A process according to claim 37, wherein, $Y_1$ and $Y_2$ taken together form a carbonyl group.

44. A process according to claim 37, wherein R is benzoyl, $R_1$ is acetyl and $R_2$ is a hydroxy protecting group.

45. A process according to claim 44, wherein $R_2$ is selected from the group consisting of ethoxyethyl, triethylsilyl, triisopropylsilyl, t-butyldimethylsilyl, t-butyldiphenylsilyl, benzyl and tert-butyloxycarbonyl.

46. A process according to claim 37, wherein R is benzoyl, $R_1$ is acetyl and $R_2$ is a hydrogen.

47. A process according to claim 37, wherein R is benzoyl and wherein $R_1$ and $R_2$ are both hydrogen.

48. A process according to claim 37, wherein R is benzoyl and wherein $R_1$ and $R_2$ are both a hydroxy protecting group.

49. A process according to claim 37, wherein $R_1$ and $R_2$ are selected from the group consisting of ethoxyethyl, triethylsilyl, triisopropylsilyl, t-butyldimethylsilyl, t-butyldiphenylsilyl, benzyl and tert-butyloxycarbonyl.

50. A process according to claim 37, wherein R is tert-butyloxycarbonyl, $R_1$ is acetyl and $R_2$ is a hydroxy protecting group.

51. A process according to claim 50, wherein $R_2$ is selected from the group consisting of ethoxyethyl, triethylsilyl, triisopropylsilyl, t-butyldimethylsilyl, t-butyldiphenylsilyl, benzyl and tert-butyloxycarbonyl.

52. A process according to claim 37, wherein R is tert-butyloxycarbonyl, $R_1$ is acetyl and $R_2$ is a hydrogen.

53. A process according to claim 37, wherein R is tert-butyloxycarbonyl and wherein $R_1$ and $R_2$ are both hydrogen.

54. A process according to claim 37, wherein R is tert-butyloxycarbonyl and wherein $R_1$ and $R_2$ are both a hydroxy protecting group.

55. A process according to claim 54, wherein $R_1$ and $R_2$ are selected from the group consisting of ethoxyethyl, triethylsilyl, triisopropylsilyl, t-butyldimethylsilyl, t-butyldiphenylsilyl, benzyl and tert-butyloxycarbonyl.

56. A process according to claim 37, wherein L is a cleavable chiral linker.

57. A process according to claim 37, wherein L is a chiral tartaric diester acetonide having enantiomerically enriched or substantially pure (R,R) or (S,S) stereochemistry, or a mixture of (R,R) and (S,S) enantiomers including racemic mixtures.

58. A process according to claim 37, wherein L is a chiral trans-1,2-cyclohexane di(carboxylate ester) having enantiomerically enriched or substantially pure (R,R) or (S,S) stereochemistry or a mixture of (R,R) and (S,S) enantiomers including racemic mixtures.

59. A process according to claim 37, wherein L is a chiral 1,1'-binaphthyl-2,2'-di(carboxylate ester) having enantiomerically enriched or substantially pure (R) or (S) stereochemistry or a mixture of (R) and (S) enantiomers including racemic mixtures.

60. A process according to claim 37, wherein L is of formula

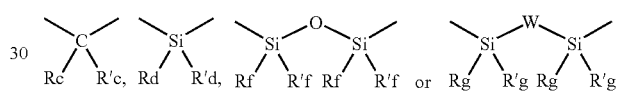

wherein Rc and R'c, identical or different are alkyl, aryl or hydrogen, Rd and R'd, identical or different are alkyl, aryl or hydrogen, Rf and R'f, identical or different are alkyl, aryl or hydrogen, Rg and R'g, identical or different are alkyl, aryl or hydrogen; W is an alkyl.

61. A process according to claim 37, wherein L is —$CH_2$—($C_6H_5$)—($CH_2$)—.

62. A process for producing a compound of formula

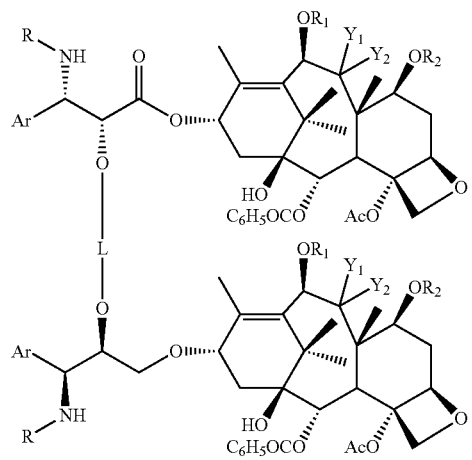

comprising treating a compound of formula

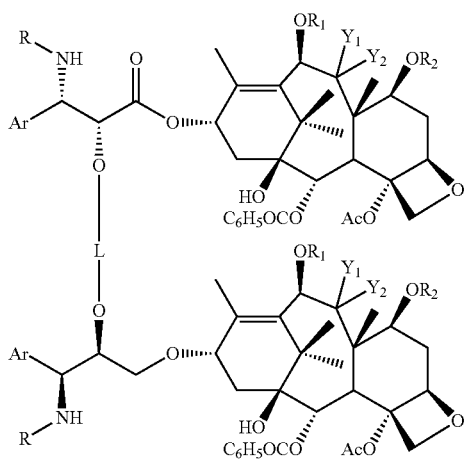

with an oxidizing agent; wherein Ar is an aryl, R is an acyl, $R_1$, and $R_2$, identical or different, are independently acyl, hydrogen or a hydroxy protecting group, L is a cleavable linker.

63. The process of claim 62 wherein the oxidizing agent is selected from the group consisting of o-iodoxybenzoic acid (IBX), Dess-Martin periodinane, iodosobenzene, iodoazobenzene diacetate, Jone's reagent, pyridinium dichromate, pyridinium chlorochromate, potassium permanganate and Swern reagent.

64. A process of preparing paclitaxel comprising the comprising the steps of cleaving the linker L of a compound of formula

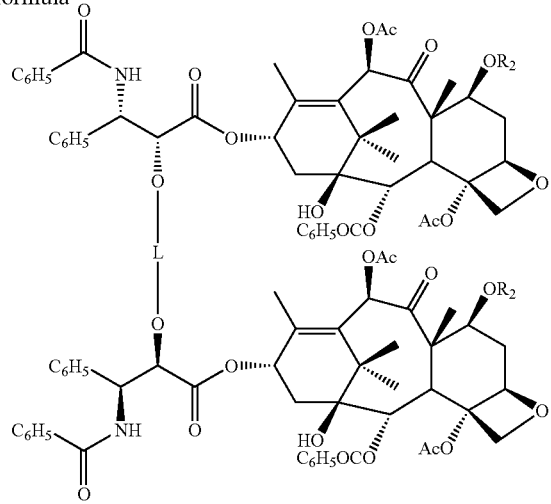

wherein $R_2$ is a hydroxy protecting group and L is a cleavable linker; to release paclitaxel protected at the 7-hydroxyl position

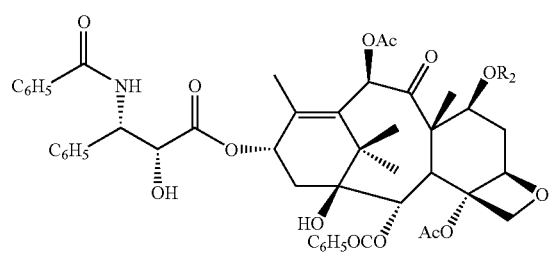

and deprotecting the hydroxy groups at the 7-hydroxyl position to obtain paclitaxel

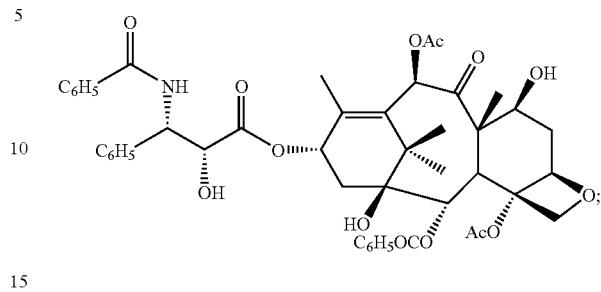

or deprotecting the hydroxy groups at the 7-hydroxy positions of a compound of formula:

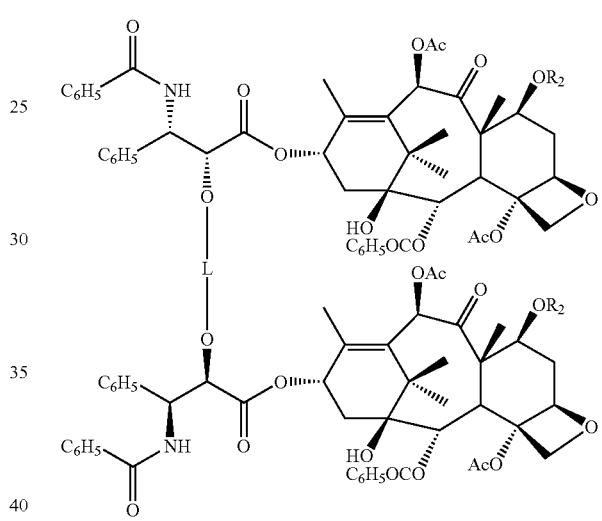

wherein $R_2$ is a hydroxy protecting group and L is a cleavable linker; to release a paclitaxel dimer of formula:

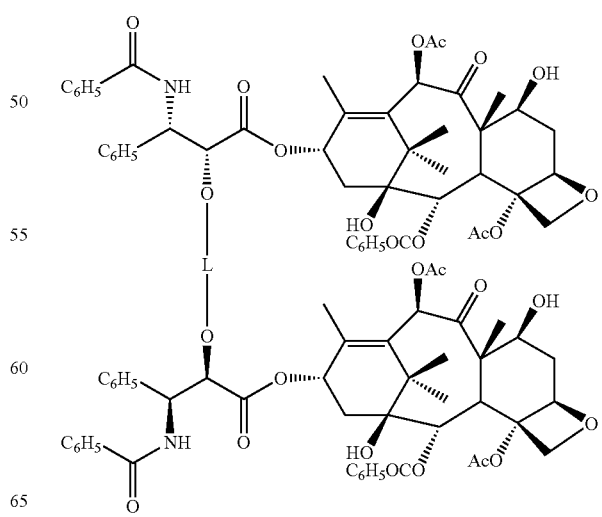

wherein L is as defined previously; and cleaving the linker L to release paclitaxel:

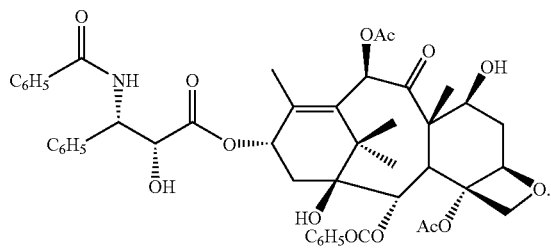

65. The process of claim 64 wherein paclitaxel is obtained in the anhydrous form from crystallization in non protic solvents or paclitaxel is obtained in the trihydrate form from crystallization in protic solvents.

66. A process of preparing docetaxel comprising the steps of cleaving the linker L of a compound of formula

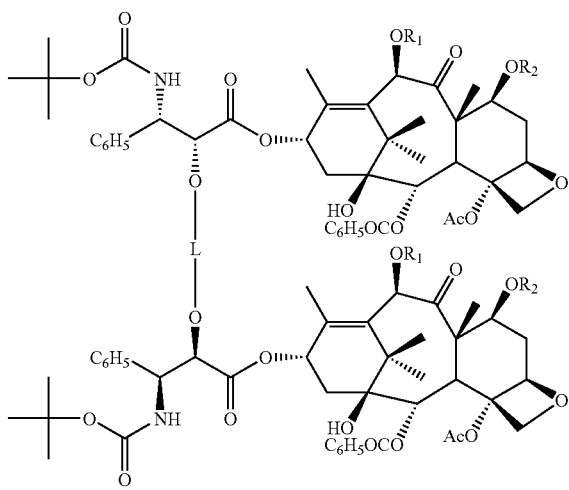

wherein $R_1$, and $R_2$, identical or different, are a hydroxy protecting group, L is a cleavable linker to release docetaxel protected at the 7 and 10-hydroxy positions

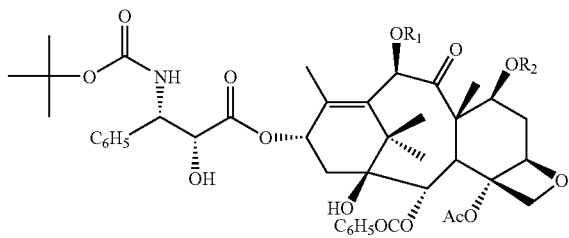

and deprotecting the hydroxy groups at the 7 and 10-hydroxy positions to obtain docetaxel or
deprotecting the hydroxy groups at the 7 and 10-hydroxy positions of a compound of formula:

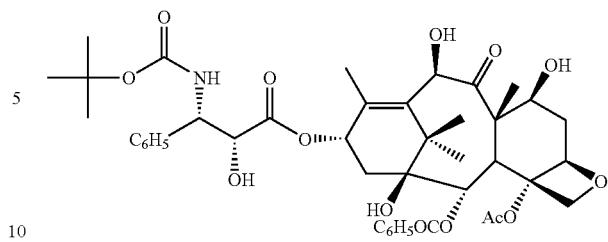

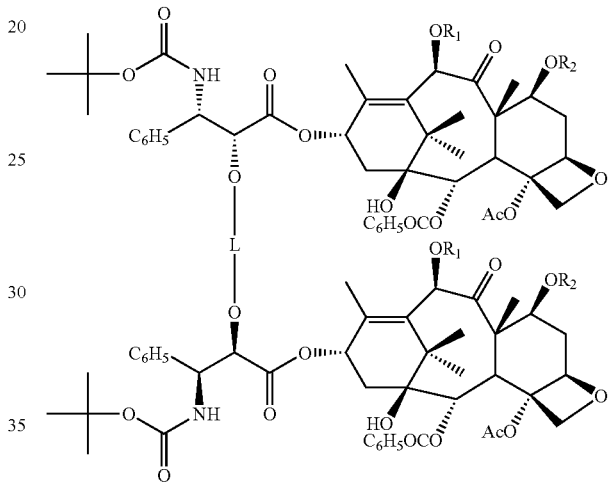

wherein $R_1$, and $R_2$, identical or different, are a hydroxy protecting group, L is a cleavable linker to release docetaxel dimer of formula

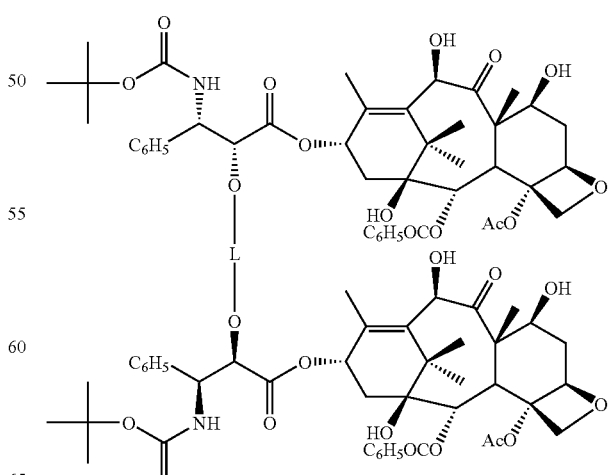

wherein L is as defined above; and cleaving the linker L to release docetaxel of formula

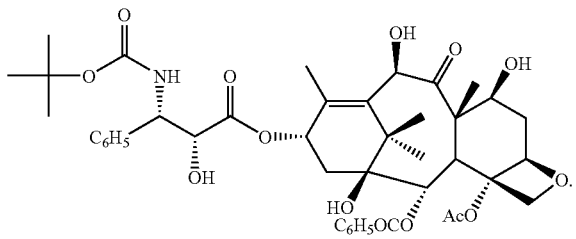

67. The process of claim 66 wherein docetaxel is obtained in the anhydrous form from crystallization in non protic solvents or docetaxel is obtained in the trihydrate form from crystallization in protic solvents.

68. The compound according to claim 1, wherein said cleavable linker L is selected from the group consisting of hydrolysable ketals, acetals, silyl, esters, diesters, and hydrogenolyzable benzyl group.

69. The process according to claim 35, wherein said cleavable linker L is selected from the group consisting of hydrolysable ketals, acetals, silyl, esters, diesters, and hydrogenolyzable benzyl group.

* * * * *